(12) United States Patent
Kulkarni et al.

(10) Patent No.: US 8,611,639 B2
(45) Date of Patent: Dec. 17, 2013

(54) SEMICONDUCTOR DEVICE PROPERTY EXTRACTION, GENERATION, VISUALIZATION, AND MONITORING METHODS

(75) Inventors: Ashok Kulkarni, San Jose, CA (US); Chien-Huei (Adam) Chen, San Jose, CA (US); Cecelia Campochiaro, Sunnyvale, CA (US); Richard Wallingford, San Jose, CA (US); Yong Zhang, Cupertino, CA (US); Brian Duffy, San Jose, CA (US)

(73) Assignee: KLA-Tencor Technologies Corp, Milpitas, CA (US)

( * ) Notice: Subject to any disclaimer, the term of this patent is extended or adjusted under 35 U.S.C. 154(b) by 1409 days.

(21) Appl. No.: 11/830,485

(22) Filed: Jul. 30, 2007

(65) Prior Publication Data

US 2009/0037134 A1    Feb. 5, 2009

(51) Int. Cl.
*G06K 9/00* (2006.01)
(52) U.S. Cl.
USPC ............ 382/149; 382/145; 382/147; 382/150
(58) Field of Classification Search
USPC .......................................... 382/145, 147, 149
See application file for complete search history.

(56) References Cited

U.S. PATENT DOCUMENTS

| | | | |
|---|---|---|---|
| 4,845,558 A | 7/1989 | Tsai et al. | |
| 4,898,471 A | 2/1990 | Vaught et al. | |
| 5,355,212 A | 10/1994 | Wells et al. | |
| 5,555,315 A | 9/1996 | Itakura | |
| 5,608,453 A | 3/1997 | Gerber et al. | |
| 5,625,451 A | 4/1997 | Schiff et al. | |
| 5,909,276 A | 6/1999 | Kinney et al. | |
| 5,991,699 A | 11/1999 | Kulkarni et al. | |
| 6,201,601 B1 | 3/2001 | Vaez-Iravani et al. | |
| 6,271,916 B1 | 8/2001 | Marxer et al. | |
| 6,538,730 B2 | 3/2003 | Vaez-Iravani et al. | |
| 6,552,337 B1 | 4/2003 | Cho et al. | |
| 6,563,577 B2 | 5/2003 | Oomori et al. | |

(Continued)

FOREIGN PATENT DOCUMENTS

| | | |
|---|---|---|
| JP | 2001-304842 | 10/2001 |
| JP | 2006-170907 | 6/2006 |

(Continued)

OTHER PUBLICATIONS

U.S. Appl. No. 60/974,030 (Bhaskar et al.) entitled Systems and Methods for Creating Persistent Data for a Wafer and for Using Persistent Data for Inspection-Related Functions filed Sep. 20, 2007.

(Continued)

*Primary Examiner* — Anand Bhatnagar
*Assistant Examiner* — Soo Park
(74) *Attorney, Agent, or Firm* — Ann Marie Mewherter

(57) ABSTRACT

Various methods, carrier media, and systems for monitoring a characteristic of a specimen are provided. One computer-implemented method for monitoring a characteristic of a specimen includes determining a property of individual pixels on the specimen using output generated by inspecting the specimen with an inspection system. The method also includes determining a characteristic of individual regions on the specimen using the properties of the individual pixels in the individual regions. The method further includes monitoring the characteristic of the specimen based on the characteristics of the individual regions.

38 Claims, 7 Drawing Sheets

(56) References Cited

U.S. PATENT DOCUMENTS

| | | | |
|---|---|---|---|
| 6,596,553 | B1 | 7/2003 | Lin et al. |
| 6,603,877 | B1 | 8/2003 | Bishop et al. |
| 6,636,031 | B1 | 10/2003 | Kenmochi et al. |
| 6,718,526 | B1 | 4/2004 | Eldredge et al. |
| 6,781,688 | B2 | 8/2004 | Kren et al. |
| 6,794,885 | B1 | 9/2004 | Yasumoto |
| 6,858,859 | B2 | 2/2005 | Kusunose |
| 6,917,419 | B2 | 7/2005 | Fielden et al. |
| 6,919,957 | B2 | 7/2005 | Nikoonahad et al. |
| 7,006,886 | B1 | 2/2006 | Huet et al. |
| 7,038,773 | B2 | 5/2006 | Kuhlmann et al. |
| 7,067,819 | B2 | 6/2006 | Janik |
| 7,286,218 | B2 | 10/2007 | Tiemeyer et al. |
| 7,315,642 | B2 | 1/2008 | Bartov et al. |
| 7,349,079 | B2 | 3/2008 | Zhao et al. |
| 7,359,052 | B2 | 4/2008 | Fielden et al. |
| 7,369,233 | B2 | 5/2008 | Nikoonahad et al. |
| 7,373,277 | B1 | 5/2008 | Wu et al. |
| 7,417,722 | B2 | 8/2008 | Bills et al. |
| 2001/0033683 | A1 | 10/2001 | Tanaka et al. |
| 2002/0182760 | A1 | 12/2002 | Wack et al. |
| 2003/0011786 | A1 | 1/2003 | Levy et al. |
| 2003/0116717 | A1 | 6/2003 | Knippelmeyer |
| 2003/0210393 | A1 | 11/2003 | Vaez-Iravani et al. |
| 2003/0219153 | A1* | 11/2003 | Levin et al. ............... 382/141 |
| 2003/0228050 | A1 | 12/2003 | Geshel et al. |
| 2004/0095575 | A1 | 5/2004 | Woo et al. |
| 2004/0151393 | A1 | 8/2004 | Kurauchi et al. |
| 2004/0206891 | A1 | 10/2004 | Ma et al. |
| 2004/0243635 | A1 | 12/2004 | Christophersen et al. |
| 2004/0252879 | A1 | 12/2004 | Tiemeyer et al. |
| 2005/0094864 | A1 | 5/2005 | Xu et al. |
| 2005/0109938 | A1* | 5/2005 | Miyai et al. ............... 250/311 |
| 2005/0128472 | A1 | 6/2005 | Shibata et al. |
| 2005/0252752 | A1 | 11/2005 | Fielden et al. |
| 2006/0062445 | A1 | 3/2006 | Verma et al. |
| 2006/0133661 | A1 | 6/2006 | Takeda et al. |
| 2006/0142971 | A1* | 6/2006 | Reich et al. ............... 702/150 |
| 2006/0181700 | A1 | 8/2006 | Andrews et al. |
| 2006/0192948 | A1 | 8/2006 | Judell et al. |
| 2006/0192949 | A1 | 8/2006 | Bills et al. |
| 2006/0192950 | A1 | 8/2006 | Judelle et al. |
| 2006/0256326 | A1 | 11/2006 | Bills et al. |
| 2006/0290923 | A1 | 12/2006 | Nakano et al. |
| 2007/0024998 | A1 | 2/2007 | Bills et al. |
| 2007/0156379 | A1* | 7/2007 | Kulkarni et al. ............... 703/14 |
| 2007/0201018 | A1 | 8/2007 | Takeda et al. |
| 2007/0252977 | A1 | 11/2007 | Baran et al. |
| 2007/0288219 | A1 | 12/2007 | Zafar et al. |
| 2008/0013083 | A1 | 1/2008 | Kirk et al. |
| 2008/0018887 | A1 | 1/2008 | Chen et al. |

FOREIGN PATENT DOCUMENTS

| | | |
|---|---|---|
| JP | 2007-033433 | 2/2007 |
| KR | 10-2001-0001224 | 1/2001 |
| WO | WO 2006/066135 | 6/2006 |
| WO | WO 2006/066136 | 6/2006 |
| WO | WO 2006/066137 | 6/2006 |
| WO | WO 2006/066138 | 6/2006 |
| WO | WO 2006/066139 | 6/2006 |
| WO | WO 2006/066205 | 6/2006 |
| WO | WO 2006/066206 | 6/2006 |
| WO | WO 2006/066207 | 6/2006 |
| WO | WO 2006/066255 | 6/2006 |

OTHER PUBLICATIONS

U.S. Appl. No. 61/074,065 (Chen et al.) entitled Computer-Implemented Methods, Computer-Readable Media, and Systems for Determining One of More Characteristics of a Wafer filed Jun. 19, 2008.

U.S. Appl. No. 12/128,426 (Biellak et al.) entitled Systems and Methods for Determining Two or More Characteristics of a Wafer filed Jul. 24, 2008.

U.S. Appl. No. 12/179,260 (Reich et al.) entitled Computer-Implemented Methods for Inspecting and/or Classifying a Wafer filed Jul. 24, 2008.

International Search Report and Written Opinion for PCT/US08/075867 mailed Feb. 17, 2009.

International Search Report and Written Opinion for PCT/US08/071587 mailed Dec. 17, 2008.

U.S. Appl. No. 60/868,769, filed Dec. 6, 2006, Fouquet et al.

U.S. Appl. No. 60/870,724, filed Dec. 19, 2006, Kulkarni et al.

U.S. Appl. No. 60/883,617, filed Jan. 5, 2007, Park et al.

U.S. Appl. No. 11/680,152, filed Feb. 28, 2007, Chen et al.

U.S. Appl. No. 11/683,696, filed Mar. 8, 2007, Chen et al.

U.S. Appl. No. 11/855,573, filed Sep. 14, 2007, Wu et al.

U.S. Appl. No. 11/855,851, filed Sep. 14, 2007, Wu et al.

McMillan, Wayne; "Surfscan SP2: Enabling Cost-Effective Production and the 65nm Node and Beyond," Yield Management Solutions, Summer 2004, pp. 14-23.

Larson, C. Thomas; "Measuring Haze on Deposited Metals with Light-Scattering-Based Inspection Systems," MICRO (Sep. 1996), pp. 31-38.

Stover, John C. Optical Scattering: Measurement and Analysis, SPIE Optical Engineering Press, Bellingham, WA (1995).

Elson et al. "Relationship of the total integrated scattering from multilayer-coated optics to angle of incidence, polarization, correlation length, and roughness cross-correlation properties," J.M. et al. Applied Optics, 22, 3207 (1983).

Scheer, B.W. "Development of a physical haze and microroughness standard," SPIE vol. 2862, pp. 78-95 (1996).

Griffith, J.E. et al.; "Characterization of Scanning Probe Tips for Linewidth Measurement," J. Vac. Sci. Technol. B 9(6), Nov./Dec. 1991, pp. 3586-3589.

Malik, Igor J. et al. "Surface Roughness of Si Wafers: Correlating AFM and Haze Measurements," Semiconductor Silicon/1994: Seventh International Symposium on Silicon Materials Science and Technology, ed. H.R. Huff, W. Bergholz and K. Sumino, The Electrochemical Society, Inc. PV 94-10, Pennington, NJ, 1994, p. 1182.

Marx, Egon et al. "Power spectral densities: A multiple technique study of different Si wafer surfaces," J. Vac. Sci. Technol. B 20(1), Jan./Feb. 2002, pp. 31-41.

International Search Report for PCT/US07/61912 dated Feb. 25, 2008.

Holsteynes et al. "The use of unpatterned wafer inspection for immersion lithography defectivity studies." Apr. 2006.

Nemoto et al. "Impact of Silicon Surface Roughness on Device Performance and Novel Roughness Measurement Method," IEEE/SEMI Advanced Semiconductor Manufacturing Conference, 2007.

Chen et al. "Laser Scattering Correlation with Polysilicon Surface Roughness and Impact on Electical Performance," ISSM 2006.

International Search Report and Written Opinion for PCT/US07/69465 mailed on Sep. 17, 2008.

International Application No. PCT/US05/45781 filed on Dec. 12, 2005.

Notification of Reason for Rejection for Japanese Patent Application No. 2010-520152 mailed Jun. 4, 2013.

* cited by examiner

SEMICONDUCTOR DEVICE PROPERTY EXTRACTION, GENERATION, VISUALIZATION, AND MONITORING METHODS

BACKGROUND OF THE INVENTION

1. Field of the Invention

The present invention generally relates to methods, carrier media, and systems for monitoring a characteristic of a specimen. Certain embodiments relate to determining a characteristic of individual regions on a specimen using properties of individual pixels in the individual regions and monitoring a characteristic of the specimen based on the characteristics of the individual regions.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

Many different types of inspection tools have been developed for the inspection of semiconductor wafers. The inspection tools may be categorized generally according to the types of specimens that they are designed to inspect. For example, one category of inspection tools is generally designed to inspect unpatterned semiconductor wafers. Since these tools are optimized for inspecting unpatterned wafers, these tools are generally not capable of inspecting patterned wafers for a number of reasons. For example, many unpatterned wafer inspection tools are configured such that all of the light collected by a lens or another collector is directed to a single detector that generates a single output signal representative of all of the light collected by the lens. Therefore, light scattered from patterns or other features on the specimen will be combined with other scattered light. As such, the single detector may become saturated and, consequently, will not yield signals that can be analyzed for defect detection. In addition, even if the single detector does not become saturated, the light scattered from patterns or other features on the wafer cannot be separated from other scattered light thereby hindering, if not preventing, defect detection based on the other scattered light.

Patterned wafer inspection is of particular interest and importance to the semiconductor industry because processed semiconductor wafers usually have a pattern of features formed thereon. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the process tool. Inspection of patterned wafers after such processing is, therefore, important to accurately detect defects that may have been formed on the wafer during, or as a result of, processing.

Many inspection tools have been developed for patterned wafer inspection. For example, U.S. Pat. No. 5,355,212 to Wells et al., which is incorporated by reference as if fully set forth herein, discloses a process for inspecting patterned wafers. In such processes, scattered light is detected thereby producing data, and periodic pattern features are removed from the data by mapping features from a plurality of periodically repeating die on the surface to a single die map and looking for overlapping features. Unique, nonoverlapping features are determined to correspond to particles and defects. In another example, U.S. Pat. No. 4,898,471 to Stonestrom et al. discloses particle detection on patterned wafers and the like. In such particle detection, a light collection system collects light scattered from the surface, and a detector produces an electrical signal corresponding to the intensity of scattered light that is collected. A processor constructs templates from the electrical signal corresponding to individual die and compares the templates to identify particles. A reference template is constantly updated so that comparisons are between adjacent die. In one embodiment, the templates are made up of registered positions where the signal crosses a threshold, and the comparison is between corresponding positions to eliminate periodic pattern features, leaving only positions representing particles.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined from currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic (s)), the measurements of the one or more characteristics of the wafer may be used to alter one or more parameters of the process such that additional wafers manufactured by the process have acceptable characteristic(s).

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on the wafer such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Furthermore, using metrology tools to measure characteristics across the wafer for inline monitoring and control applications is not feasible due to the time in which such measurements can be performed. In particular, metrology measurements performed by currently available metrology tools such as surface roughness, resistivity, film thickness, etc. are not suitable for high sampling of wafers for inline monitoring since the measurements will impact (e.g., increase) cycle time in production.

Accordingly, it would be advantageous to develop methods, carrier media, and systems that can be used for monitoring a characteristic of a specimen using output generated by an inspection system and for identifying systematic process issues and defects on the specimen.

SUMMARY OF THE INVENTION

The following description of various embodiments of methods, carrier media, and systems is not to be construed in any way as limiting the subject matter of the appended claims. In general, some of the embodiments described herein relate to semiconductor device property extraction, generation, visualization, and monitoring methods.

One embodiment relates to a computer-implemented method for monitoring a characteristic of a specimen. The method includes determining a property of individual pixels on the specimen using output generated by inspecting the specimen with an inspection system. The method also includes determining a characteristic of individual regions on the specimen using the properties of the individual pixels in the individual regions. The method further includes monitoring the characteristic of the specimen based on the characteristics of the individual regions.

In one embodiment, each of the individual regions has an area that is greater than an area of one individual pixel and is less than an area of the specimen. In another embodiment, the individual regions have a rectangular shape, and the individual regions form a two-dimensional grid on the specimen. In some embodiments, the specimen includes a patterned wafer.

In one embodiment, the method includes identifying one or more of the individual regions having unique characteristics. In another embodiment, the method includes selecting one or more of the individual regions having unique characteristics for metrology. In an additional embodiment, the method includes determining one or more locations on the specimen corresponding to one or more of the individual regions having unique characteristics and generating information about the one or more locations that can be used to perform one or more measurements at the one or more locations.

In one embodiment, the characteristic of the specimen includes a specimen-level signature in the characteristics of the individual regions. In another embodiment, the characteristic of the specimen includes a die-level signature in the characteristics of the individual regions. In some embodiments, the method includes determining potential process problems based on the characteristics of the individual regions and generating output illustrating the potential process problems. In a further embodiment, the method includes detecting defects on the specimen using the output while the monitoring is performed.

In one embodiment, the properties of the individual pixels used to determine the characteristic of each of the individual regions include the properties of all of the individual pixels within each of the individual regions. In another embodiment, the characteristic of the individual regions includes a statistic of the properties of the individual pixels within the individual regions. In an additional embodiment, the characteristic of the individual regions includes a distribution of the properties of the individual pixels within the individual regions. In a further embodiment, the characteristic of the individual regions includes a property of a distribution of the properties of the individual pixels within the individual regions. In some embodiments, the characteristic of the individual regions includes a property of a distribution of the properties of the individual pixels within the individual regions and a location corresponding to the property of the distribution.

In one embodiment, a portion of the individual regions corresponds to a die on the specimen. In one such embodiment, the method includes aligning the portion of the individual regions to a different portion of the individual regions corresponding to a different die on the specimen. In another such embodiment, the method includes aligning the portion of the individual regions to a reference die. In some embodiments, different portions of the individual regions correspond to different dies on the specimen, and the method includes aligning the different portions to a common reference grid. In a further embodiment, the property of the individual pixels includes a differential between the properties of the individual pixels located in adjacent dies on the specimen at the same within die position. In one such embodiment, the characteristic of the individual regions includes a distribution of the differentials of the individual pixels within the individual regions.

In one embodiment, determining the characteristic of the individual regions includes separating the individual pixels into groups based on design context associated with the individual pixels. In one such embodiment the characteristic of the individual regions includes a characteristic of the groups.

In some embodiments, the method includes generating output illustrating the property of each of the individual pixels corresponding to one of the individual regions as a function of position across the one of the individual regions. In another embodiment, the method includes comparing the properties of the individual pixels to a threshold value and generating output indicating the individual pixels on the specimen having a property that is above the threshold value and the individual pixels on the specimen having a property that is below the threshold value.

In one embodiment, the characteristic of the specimen includes the characteristic of the individual regions as a function of position across the specimen. In one such embodiment, monitoring the characteristic of the specimen includes determining similarities between the characteristic of the specimen and a reference. In another embodiment, the characteristic of the specimen includes the characteristics of the individual regions corresponding to at least one die on the specimen combined with the characteristics of the individual regions corresponding to at least one additional die on the specimen. In one such embodiment, monitoring the characteristic of the specimen includes determining similarities between the combined characteristics and a reference.

In one embodiment, monitoring the characteristic of the specimen includes monitoring the characteristic of the specimen on a specimen-to-specimen basis or a lot-to-lot basis by comparing the characteristic of the specimen to one or more control limits. In another embodiment, monitoring the characteristic of the specimen includes comparing the characteristic of the specimen to one or more control limits and determining locations on the specimen at which the characteristic of the specimen exceeds the one or more control limits. In one such embodiment, the method includes generating information about the locations that can be used to perform one or more measurements at the locations.

In one embodiment, the method includes determining if the properties of the individual pixels within two or more die on the specimen are correlated. In another embodiment, the method includes identifying portions of two or more die on the specimen in which the properties of the individual pixels are correlated as locations of a potential systematic defect causing mechanism on the specimen. In an additional embodiment, the method includes identifying different portions of die on the specimen having different design context and determining if the properties of the individual pixels within the different portions having the same design context are correlated. In one such embodiment, the method also includes generating output illustrating the different portions having properties that are correlated.

In one embodiment, monitoring the characteristic of the specimen includes determining if the characteristics of the individual regions within two or more die on the specimen are correlated. In another embodiment, monitoring the characteristic of the specimen includes identifying portions of two or more die on the specimen in which the characteristics of the individual regions are correlated as locations of a potential systematic defect causing mechanism on the specimen. In an additional embodiment, monitoring the characteristic of the specimen includes identifying different portions of die on the specimen having different design context and determining if the characteristics of the individual regions within the different portions having the same design context are correlated. In one such embodiment, the method includes generating output illustrating the different portions having characteristics of the individual regions that are correlated. In some embodiments, the method includes stacking two or more individual dies on the specimen and displaying a stacked die map.

In one embodiment, the method includes constructing a signature image of the specimen. In one such embodiment, each pixel of the signature image represents a selected characteristic of the individual regions. In another such embodiment, the method includes displaying two or more signature images side by side. In an additional such embodiment, the method includes displaying one or more signature images overlaid on a wafer map of defects.

Each of the steps of each of the embodiments of the method described above may be further performed as described herein. Each of the embodiments described above may include any other step(s) described herein. In addition, each of the embodiments of the method described above may be performed by any of the systems described herein.

Another embodiment relates to a carrier medium that includes program instructions executable on a processor for performing a method for monitoring a characteristic of a specimen. The method includes determining a property of individual pixels on the specimen using output generated by inspecting the specimen with an inspection system. The method also includes determining a characteristic of individual regions on the specimen using the properties of the individual pixels in the individual regions. The method further includes monitoring the characteristic of the specimen based on the characteristics of the individual regions. The method for which the program instructions are executable may include any other step(s) described herein.

An additional embodiment relates to a system configured to monitor a characteristic of a specimen. The system includes an inspection system configured to generate output by inspecting the specimen. The system also includes a processor configured to determine a property of individual pixels on the specimen using the output. The processor is also configured to determine a characteristic of individual regions on the specimen using the properties of the individual pixels in the individual regions. The processor is further configured to monitor the characteristic of the specimen based on the characteristics of the individual regions. The system embodiment described above may be further configured as described herein.

A further embodiment relates to a computer-implemented method for generating an image of a surface of a patterned wafer. The method includes acquiring output of an inspection system for the patterned wafer. The method also includes generating the image of the surface of the patterned wafer using the output.

In one embodiment, acquiring the output includes acquiring the output of the inspection system for the patterned wafer using optical pattern suppression. In one such embodiment, the optical pattern suppression includes Fourier filtering. In another embodiment, the acquiring step includes acquiring the output for substantially an entire surface of the patterned wafer.

In one embodiment, the image of the surface of the patterned wafer includes an image of substantially an entire surface of the patterned wafer. In another embodiment, the image of the surface of the patterned wafer is substantially free of pattern misregistration noise. In an additional embodiment, the image of the surface of the patterned wafer includes a gray scale image of intensity of light scattered from the patterned wafer. In a further embodiment, the image of the surface of the patterned wafer includes a noise map of the surface of the patterned wafer.

In one embodiment, the generating step includes determining one or more statistics for one or more regions of the patterned wafer in which the output is acquired using optical pattern suppression. In one such embodiment, the image includes a gray scale image of the one or more statistics. In another embodiment, the generating step includes dividing one or more regions of the patterned wafer in which the output is acquired using optical pattern suppression into one or more sub-regions and determining one or more statistics for the one or more sub-regions. In one such embodiment, the image includes a gray scale image of the one or more statistics.

In one embodiment, the generating step includes determining if one or more regions of the patterned wafer are not suitable for optical pattern suppression and removing images corresponding to the one or more regions from the image of the surface. In another embodiment, the generating step includes determining one or more statistics in only regions of the wafer or dies on the wafer in which the pattern is optically suppressed.

In one embodiment, generating the image includes generating noise maps of dies formed on the patterned wafer. In one such embodiment, the method includes comparing the noise maps to one or more other noise maps of dies to accept or reject individual dies on the patterned wafer. In another such embodiment, the method includes comparing the noise maps to one or more other noise maps of dies, and the one or more other noise maps include the noise maps of the dies on the patterned wafer. In an additional such embodiment, the method includes comparing the noise maps to one or more other noise maps of dies, and the one or more other noise maps include noise maps of dies on other patterned wafers. In a further such embodiment, the method includes comparing the noise maps to one or more other noise maps of dies, and the one or more other noise maps include a composite of multiple die noise maps from a full patterned wafer noise map.

In one embodiment, generating the image includes generating noise maps of dies formed on the patterned wafer, and the method includes generating a composite noise map from all of the noise maps of the dies on the patterned wafer and comparing the composite noise map to one or more other noise maps of dies. In another embodiment, the patterned wafer includes a test patterned wafer, and generating the image includes generating noise maps of dies formed on the patterned wafer. In one such embodiment, the method includes generating a composite noise map of multiple die noise maps from a full patterned wafer noise map and storing the composite noise map as a golden die noise map for comparison to the noise maps of the dies formed on the test patterned wafer.

In some embodiments, generating the image includes generating noise maps of dies formed on the patterned wafer, and the method includes displaying the noise maps with design information overlaid thereon such that noise is displayed as a function of die functional region. In another embodiment, the image of the surface of the patterned wafer includes a noise map of the surface of the patterned wafer, and the method includes displaying the noise map with one or more attributes determined by the inspection system overlaid thereon. In a further embodiment, the image of the surface of the patterned wafer includes a noise map of the surface of the patterned wafer, and the method includes simultaneously displaying the noise map and one or more attributes determined by the inspection system.

In one embodiment, the method includes determining if a defect signature is present in the image without applying a threshold for defect detection to the image. In another embodiment, the method includes determining if a defect signature is present in the image without tuning a defect detection algorithm. In an additional embodiment, the method includes applying spatial signature analysis to the image to determine if a defect signature is present in the image. In a further embodiment, the method includes determining if a process signature is present in the image without applying a threshold for defect detection to the image. In some embodiments, the method includes identifying a defect signature present in the image without applying a threshold for defect detection to the image. In additional embodiments, the method includes identifying a process signature present in the image without applying a threshold for defect detection to the image.

In one embodiment, the method includes determining an optics mode of the inspection system to be used for the acquiring step such that the image can be used for detecting a selected defect signature. In another embodiment, the method includes determining, without tuning a defect detection algorithm, an optics mode of the inspection system to be used for the acquiring step such that the image can be used for detecting a selected defect signature.

In one embodiment, the method includes performing the acquiring step using more than one optics mode of the inspection system, generating more than one image of the surface of the patterned wafer using the output acquired using the more than one optics mode, and using the more than one image to determine an optics mode of the inspection system to be used for the acquiring step such that the image can be used for detecting a selected defect signature.

In another embodiment, the image of the surface of the patterned wafer includes a noise map of the surface of the patterned wafer. The method includes performing the acquiring step using more than one optical configuration of the inspection system. The method also includes generating more than one noise map of the surface of the patterned wafer using the output acquired using the more than one optical configuration. In addition, the method includes using the more than one noise map to identify wafer-scale process variation as a function of the more than one optical configuration. The method further includes using the wafer-scale process variation as a function of the more than one optical configuration to identify a best optics mode for the combination of the inspection system and the patterned wafer.

In an additional embodiment, the image of the surface of the patterned wafer includes a noise map of substantially an entire surface of a test patterned wafer on which a process was performed. The method includes performing the acquiring step for multiple patterned wafers on which the process was performed using one or more different parameters of the process. The method also includes generating noise maps of the surfaces of the multiple patterned wafers using the output. In addition, the method includes storing the noise maps of the surfaces of the multiple patterned wafers as a function of the one or more different parameters. The method further includes comparing the noise map for substantially the entire surface of the test patterned wafer with the stored noise maps to determine one or more characteristics of the process performed on the test patterned wafer.

In some embodiments, the method includes tuning one or more optical parameters of an inspection recipe used for the acquiring step by performing the acquiring step and the generating step using each possible optical configuration of the inspection system and using the images corresponding to each possible optical configuration to select an optical configuration for the inspection recipe based on a presence or non-presence of defect signatures in each of the images.

In a further embodiment, the acquiring step is performed using a predetermined optical configuration of the inspection system. In one such embodiment, the method includes tuning one or more parameters of a defect detection algorithm of an inspection recipe by matching a presence or non-presence of defect signatures in the image to output of the defect detection algorithm.

In one embodiment, the image of the surface of the patterned wafer includes a noise map of the surface of the patterned wafer. In some embodiments, the method includes identifying a signature, which corresponds to only the last process performed on the patterned wafer before the acquiring step, in the noise map. In another embodiment, the method includes identifying a signature, which corresponds to only the last process performed on the patterned wafer before the acquiring step, in the noise map based on one or more other signatures corresponding to one or more other processes performed on the patterned wafer.

In an additional embodiment, the method includes identifying a signature, which corresponds to only the last process performed on the patterned wafer before the acquiring step, in the noise map by extracting one or more signatures corresponding to one or more other processes performed on the patterned wafer from the noise map. In a further embodiment, the method includes identifying a signature, which corresponds to only the last process performed on the patterned wafer before the acquiring step, in the noise map, and classifying the signature.

In one embodiment, the method includes identifying a signature, which corresponds to only the last process performed on the patterned wafer before the acquiring step, in the noise map and comparing the signature to additional signatures to determine one or more characteristics of the patterned wafer or the last process. In one such embodiment, the additional signatures are generated empirically. In another such embodiment, the additional signatures are generated by modeling of one or more process tools used to perform the last process.

In another embodiment, the method includes identifying a signature, which corresponds to only the last process performed on the patterned wafer before the acquiring step, in the noise map and determining if one or more parameters of the last process are out of process control limits based on the signature. In an additional embodiment, the method includes identifying a signature, which corresponds to only the last process performed on the patterned wafer before the acquiring step, in the noise map and controlling one or more parameters of the last process based on the signature.

In some embodiments, the method includes identifying a signature, which corresponds to only the last process performed on the patterned wafer before the acquiring step, in the noise map based on raw data acquired for the patterned wafer prior to the last process and signatures identified in the raw data. In another embodiment, the method includes identifying a signature, which corresponds to only the last process performed on the patterned wafer before the acquiring step, in the noise map and determining a root cause corresponding to the signature.

In an additional embodiment, the method includes identifying a signature, which corresponds to only the last process performed on the patterned wafer before the acquiring step, in the noise map and monitoring the process based on the signature. In a further embodiment, the method includes estimating a probability that processes other than the last process performed on the patterned wafer before the acquiring step affect the noise map. In yet another embodiment, the method includes identifying a signature in the noise map and estimating a degree to which signatures of processes other than the last process performed on the patterned wafer before the acquiring step contribute to the signature in the noise map based on optics of the inspection system used to acquire the output.

Each of the steps of each of the embodiments of the method described above may be performed as described further herein. Each of the embodiments of the method described above may include any other step(s) described herein. In addition, each of the embodiments of the method described above may be performed by any of the systems described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
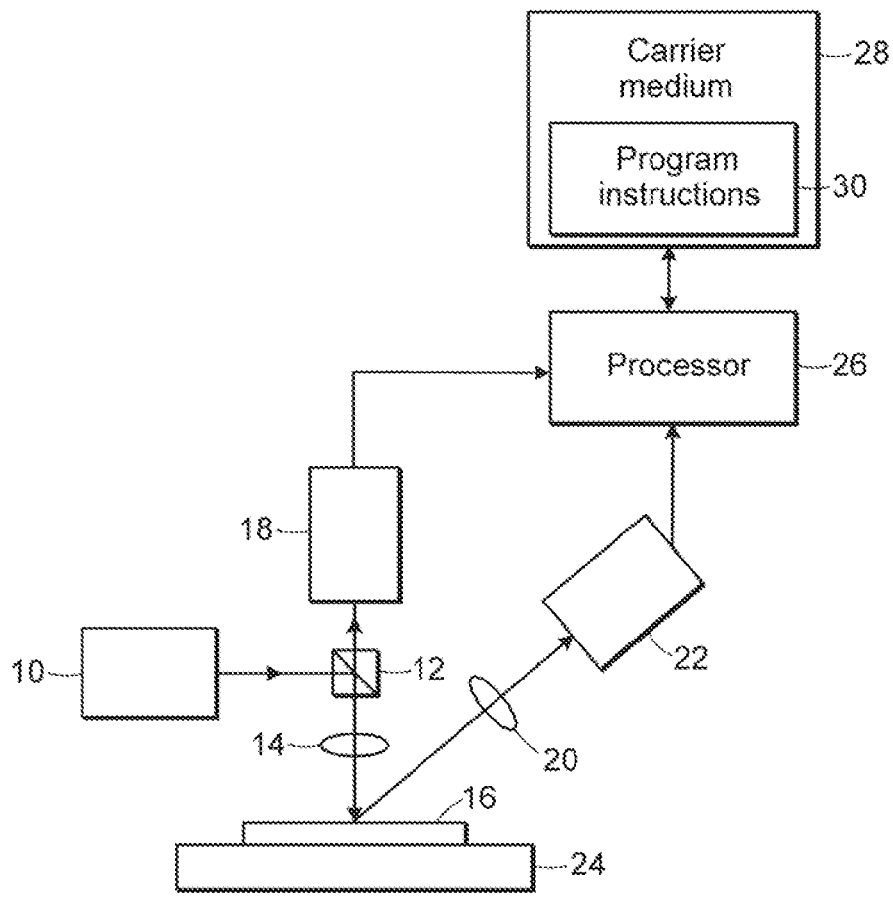
FIG. 1 is a schematic diagram illustrating a side view of one embodiment of a carrier medium that includes program instructions executable on a processor for performing a method for monitoring a characteristic of a specimen and one embodiment of a system configured to monitor a characteristic of a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer, a photomask, or a reticle. However, it is to be understood that the methods, carrier media, and systems described herein may be used for monitoring a characteristic of any other specimen known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductor material. Many different types of such layers are known in the art, and the term wafer as used herein is intended to encompass a wafer including all types of such layers.

One or more layers formed on a wafer may be patterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

The terms "reticle" and "photomask" are used interchangeably herein. A reticle generally includes a transparent substrate such as glass, borosilicate glass, and fused silica having opaque regions formed thereon. The opaque regions may be replaced by regions etched into the transparent substrate. Many different types of reticles are known in the art, and the term reticle as used herein is intended to encompass all types of reticles.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to monitor a characteristic of a specimen. The system includes an inspection system. The inspection system is configured to generate output by inspecting the specimen. It is noted that FIG. 1 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system). For some such systems, the methods described herein may be provided as optional functionality of the system (e.g., in addition to other functionality of the system). Alternatively, the system described herein may be designed "from scratch" to provide a completely new system.

The inspection system shown in FIG. 1 includes light source 10. Light source 10 may include any appropriate light source known in the art. The inspection system may also include two or more light sources (not shown). The two or more light sources may be configured similarly or differently. For example, the light sources may be configured to generate light having different characteristics (e.g., wavelength, polarization, etc.) that can be directed to a specimen at the same or different angles of incidence and at the same or different time.

Light source 10 is configured to direct light to beam splitter 12. Beam splitter 12 is configured to direct light from light source 10 to objective 14. Objective 14 is configured to focus the light from beam splitter 12 onto specimen 16 at a substantially normal angle of incidence. However, the inspection system may be configured to direct the light to the specimen at any suitable angle of incidence. Beam splitter 12 may include any appropriate optical component known in the art. Objective 14 may include any appropriate refractive optical component known in the art. In addition, although objective 14 is shown in FIG. 1 as a single refractive optical component, it is to be understood that objective 14 may include one or more refractive optical components and/or one or more reflective optical components.

The inspection system includes a collection system that includes multiple, independent detection channels. Each detection channel is configured to collect light scattered or reflected from the specimen over a unique set of collection angles. In addition, although the inspection system is described further herein as including a bright field (BF) channel and a dark field (DF) channel, it is to be understood that the inspection system may include any combination of one or more detection channels (e.g., one or more BF channels and/or one or more DF channels). Moreover, the inspection system may include a number of detection channels, and output generated by all of the detection channels or fewer than all of the detection channels may be used by a processor as described further herein. The output generated by a particular combination of detection channels that is used by a processor as described further herein may be selected based on, for example, characteristics of the specimen, characteristics of the defects of interest, and characteristics of the inspection system.

In the embodiment shown in FIG. 1, light reflected from specimen 16 is collected by objective 14 and passes through beam splitter 12 to detector 18. Detector 18 may be any appropriate detector known in the art. Detector 18 may be configured to acquire pixel-level output for specimen 16. In addition, detector 18 may be an imaging detector. Therefore, the pixel-level output generated by detector 18 may include image data. As shown in FIG. 1, objective 14 is configured to collect light specularly reflected from the specimen, and detector 18 is configured to detect light specularly reflected from the specimen. Therefore, objective 14 and detector 18 form the BF channel of the inspection system. As such, the BF channel of the inspection system may be configured to generate pixel-level output for the specimen. In addition, the BF channel of the inspection system may be configured to generate pixel-level output that includes image data.

Light scattered from specimen 16 is collected by objective 20, which directs the collected light to detector 22. Objective 20 may include any appropriate refractive optical component known in the art. In addition, although objective 20 is shown in FIG. 1 as a single refractive optical component, it is to be understood that objective 20 may include one or more refractive optical components and/or one or more reflective optical components. Objective 20 may be configured to collect light scattered from the specimen at any suitable scattering angles. In addition, the scattering angles at which objective 20 is configured to collect light scattered from the specimen may be determined based on one or more characteristics (e.g., of patterned features (not shown) or defects of interest (not shown)) of the specimen.

Detector 22 may be any appropriate detector known in the art. Detector 22 may be configured to generate pixel-level output for specimen 16. In addition, detector 22 may be an imaging detector. Therefore, the pixel-level output generated by detector 22 may include image data. As shown in FIG. 1, objective 20 is configured to collect light scattered from the specimen, and detector 22 is configured to detect light scattered from the specimen. Therefore, objective 20 and detector 22 form the DF channel of the inspection system. As such, the DF channel of the inspection system may be configured to generate pixel-level output for the specimen. In addition, the DF channel of the inspection system may be configured to generate pixel-level output that includes image data.

During generation of the output by the BF and DF channels of the inspection system, specimen 16 may be disposed on stage 24. Stage 24 may include any appropriate mechanical and/or robotic assembly known in the art (e.g., a scanning stage configured to support the specimen).

The system also includes processor 26. Processor 26 may be configured to receive output generated by inspecting the specimen. For example, processor 26 may be coupled to detectors 18 and 22 such that the processor can receive pixel-level output from detectors 18 and 22. Processor 26 may be coupled to the detectors in any suitable manner known in the art (e.g., via a transmission medium (not shown) that may include "wired" and/or "wireless" portions, via electronic components (not shown) interposed between each of the detectors and the processor, etc.).

Processor 26 is configured to determine a property of individual pixels on the specimen using the output. The processor may be configured to determine the property of the individual pixels as described further herein. The processor is also configured to determine a characteristic of individual regions on the specimen using the properties of the individual pixels in the individual regions. The processor may determine the characteristic of the individual regions as described herein. The processor is further configured to monitor the characteristic of the specimen based on the characteristics of the individual regions. The processor may monitor the characteristic of the specimen as described further herein. The processor may also be configured to perform any other step(s) of any other method(s) described herein.

Processor 26 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

The inspection system shown in FIG. 1 may also include any other suitable components (not shown) known in the art. Furthermore, the inspection system shown in FIG. 1 may be replaced with a commercially available inspection system such as the 2360, 2365, 2371, 23xx, Puma 90xx, and Puma 91xx systems that are available from KLA-Tencor, San Jose, Calif. The embodiment of the system shown in FIG. 1 may be further configured as described herein. In addition, the system may be configured to perform any other step(s) of any of the method embodiment(s) described herein. The embodiment of the system shown in FIG. 1 has all of the advantages of the method embodiments described herein.

FIG. 1 also illustrates one embodiment of carrier medium 28 that includes program instructions 30 executable on processor 26 for performing a method for monitoring a characteristic of specimen 16. The method includes determining a property of individual pixels on the specimen using output generated by inspecting the specimen with an inspection system. The property of the individual pixels may be determined as described herein. The method also includes determining a characteristic of individual regions on the specimen using the properties of the individual pixels in the individual regions. The characteristic of the individual regions may be determined as described herein. The method further includes monitoring the characteristic of the specimen based on the characteristics of the individual regions. The characteristic of the specimen may be monitored as described herein. In addition, the method for which program instructions 30 are executable may include any other step(s) of any other method (s) described herein.

Program instructions 30 implementing methods such as those described herein may be transmitted over or stored on carrier medium 28. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

As described above, the program instructions may be executable on processor 26. Therefore, the program instructions may be executable on a processor coupled to an inspection system. However, the program instructions may be executable on a processor that is not coupled to an inspection system. In this manner, the carrier medium and the processor may be configured as a "stand alone" system. The stand alone system may, however, be configured to acquire the output described above from an inspection system (e.g., from a processor or storage medium (not shown) of the inspection system). The stand-alone system may acquire the output in any manner known in the art (e.g., via a transmission medium that may include "wired" and/or "wireless" portions). In this manner, the transmission medium may serve as a data link between the processor and the inspection system. Therefore, the methods described herein may or may not include acquiring the output by performing inspection of a specimen. In other words, the methods described herein may be performed by a system that does not include an inspection system.

Another embodiment relates to a computer-implemented method for monitoring a characteristic of a specimen. In one embodiment, the specimen includes a patterned wafer. In other words, the specimen may include a wafer on which patterned features (e.g., device features, test features, etc.) are formed. However, the specimen may include any of the other specimens described herein.

In general, the embodiments described herein may include the following steps: 1) the collection of frame data, 2) the generation of wafer and die signature images from the frame data, and 3) the visualization of the wafer and die signature images. Each of these steps are described further herein.

The method includes determining a property of individual pixels on the specimen using output generated by inspecting the specimen with an inspection system. The output may include any of the output described herein. The inspection system may be configured as described herein. In addition, the output may be generated by scanning the specimen using one or more different illumination schemes and gathering response signals from every (or nearly every) pixel location on the specimen. The response signal from each pixel location can be detected by one or more detection channels. Furthermore, the output may be generated using more than one illumination scheme and more than one detection channel simultaneously (e.g., in a single scan of the specimen) or sequentially (e.g., in different scans of the specimen).

Figure 2:
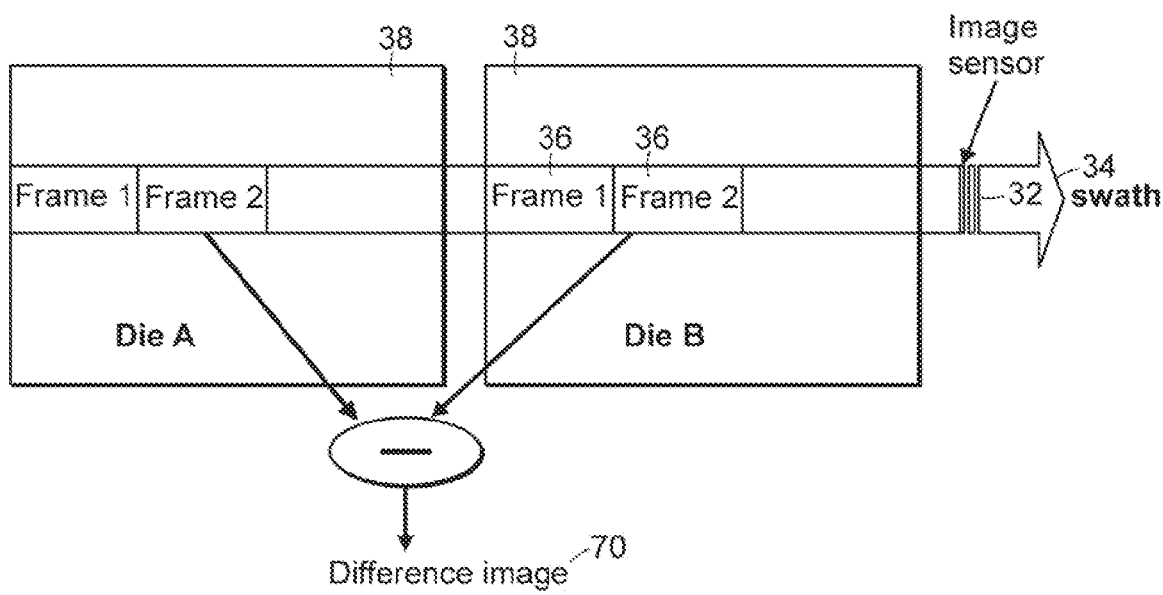
FIG. 2 is a schematic diagram illustrating a top view of one embodiment of a swath of image data divided into frames of equal size starting at each die edge.

Collection of the frame data may include collecting the frame data in the background of a regular inspection scan or as a dedicated frame data collection scan. In the later case, the inspection system may still perform a regular inspection scan, but with the threshold turned off so as to not detect any defects. During the collection of the frame data, the inspection system scans the wafer and acquires swath images. Each swath image is divided into frames of equal size starting at each die edge. For example, as shown in FIG. 2, image sensor 32 of the inspection system (not shown in FIG. 2) may acquire swath image 34. Swath image 34 is divided into frames 36 of equal size starting at the edge of each die 38. The default frame size is the same as the one used for defect detection (e.g., for some BF systems, the frame size is 512 pixels high and 1024 pixels wide). But to achieve better resolution in the final wafer signature images, the frame may be divided into sub-frames. Frame data is then extracted from the frame or sub-frame images.

In addition, it is noted that the "Individual pixels on the specimen" are not actually formed on the specimen. Instead, the "individual pixels" are individual photosensitive elements of the inspection system, each of which may detect light from the specimen and generate output responsive thereto. The output of the inspection, therefore, may include a substantial number of signals or data points, each of which corresponds to a position on the specimen at which the signal or data point was acquired. As such, the individual signals or data points in the output generated by the inspection system are also commonly referred to as "individual pixels." Since the locations on the specimen at which the individual signals or data points were generated can be determined by the inspection system or a processor coupled thereto, the "individual pixels on the specimen" can be defined as the individual signals or data points in output generated at different locations on the specimen.

Although the methods are described herein as including determining "a property" of individual pixels on a specimen, it is to be understood that the method embodiments described herein may include determining more than one property of the individual pixels on the specimen. The more than one property may include any of the properties described herein. For example, the property of the individual pixels may include the value of a signal of the individual pixels, the local mean value of the signal in an N×N pixel neighborhood around each of the individual pixels, the range or median value in such a neighborhood, or the maximum or minimum signal value in such a neighborhood. Such properties may be determined using any suitable method and/or algorithm known in the art.

In another embodiment, the property of the individual pixels is a differential between the properties of individual pixels located in adjacent dies on the specimen at the same (or substantially the same) within die position. For example, determining the property of the individual pixels may include determining a difference value between the signal for a selected pixel in a die on the specimen and the signal from the corresponding pixel in an adjacent die (or corresponding pixels in adjacent dies, one on each side of the selected die) on the specimen. The difference value may be the difference of any local property between corresponding pixels in adjacent dies. For example, the local property used to determine the differential may include N×N means, N×N ranges, local signal gradients in x and y, or gradient magnitude and phase. The differential between the properties of individual pixels may be determined using any suitable method and/or algorithm.

Figure 3:
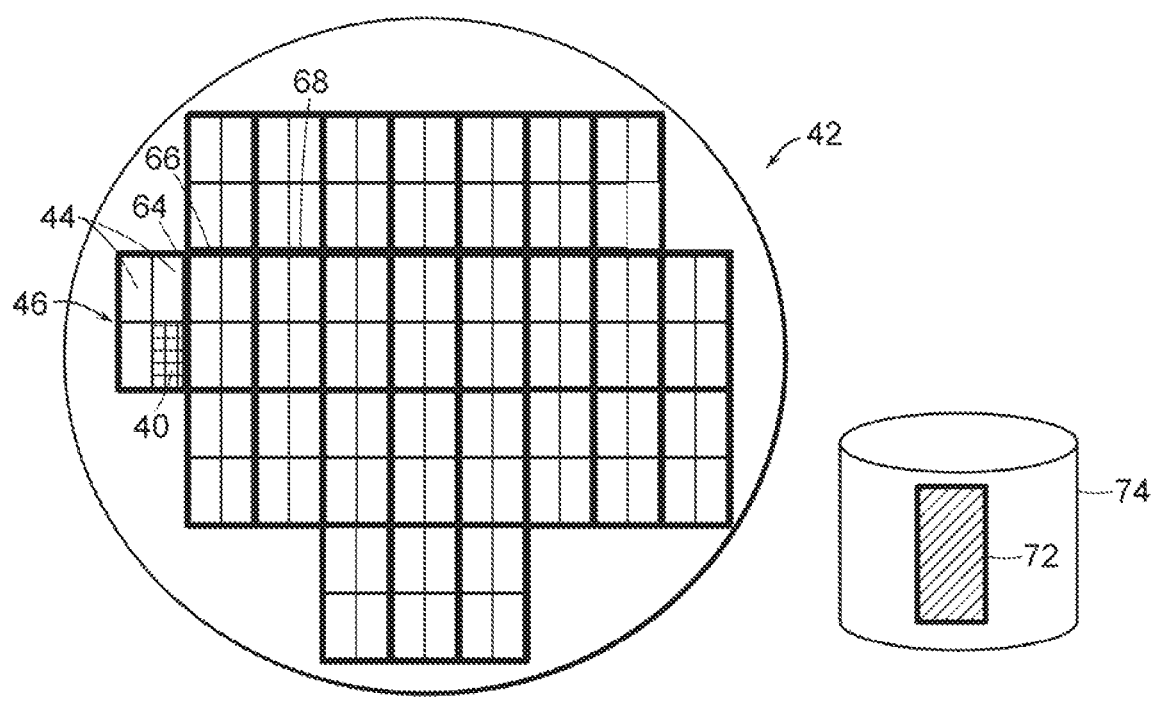
FIG. 3 is a schematic diagram illustrating a top view of one embodiment of individual pixels on a specimen corresponding to individual regions on the specimen, a portion of individual regions on a specimen that corresponds to a die on the specimen, and a reference die.

As shown in FIG. 3, individual pixels 40 on specimen 42 correspond to individual region 44 on the specimen. Although a particular number of pixels 40 is shown in individual region 44 on specimen 42 in FIG. 3, it is to be understood that the number of pixels on the specimen may include any suitable number know in the art and will generally vary depending on the configuration of the inspection system. In addition, although a particular number of individual regions 44 is shown on specimen 42 in FIG. 3, it is to be understood that the number of individual regions on the specimen may generally correspond to the number of frames on the specimen. In other words, each region may be defined as a frame in the output acquired by the inspection system. For example, a swath may include multiple frames, which may vary in size depending on parameters of the inspection system such as resolution and pixel size. In this manner, the pixels in a swath are separated based on the frames, and each frame may correspond to a different region. However, pixels in a single frame, which may also be commonly referred to as a "job," may be separated into multiple groups as described further herein. In addition, although the specimen is shown in FIG. 3 as having a particular shape, it is to be understood that the specimen may have any suitable shape and size known in the art.

As shown in FIG. 3, each of individual regions 44 has an area that is greater than an area of one individual pixel 40 and is less than an area of specimen 42. In this manner, each individual region includes at least two individual pixels on the specimen. In addition, the individual regions have an area that is less than the area of the specimen such that at least two individual regions are defined on the specimen. In some embodiments, as further shown in FIG. 3, individual regions 44 have a rectangular shape. The rectangular shape may be a rectangle or a square (i.e., the rectangular shape is not necessarily square). In one such embodiment, as shown in FIG. 3, the individual regions form two-dimensional grid 46 on the specimen. In this manner, a semiconductor die, wafer, reticle, or other specimen may be partitioned into rectangular regions that form a two-dimensional grid that can be overlaid on a specimen surface.

Figure 4:
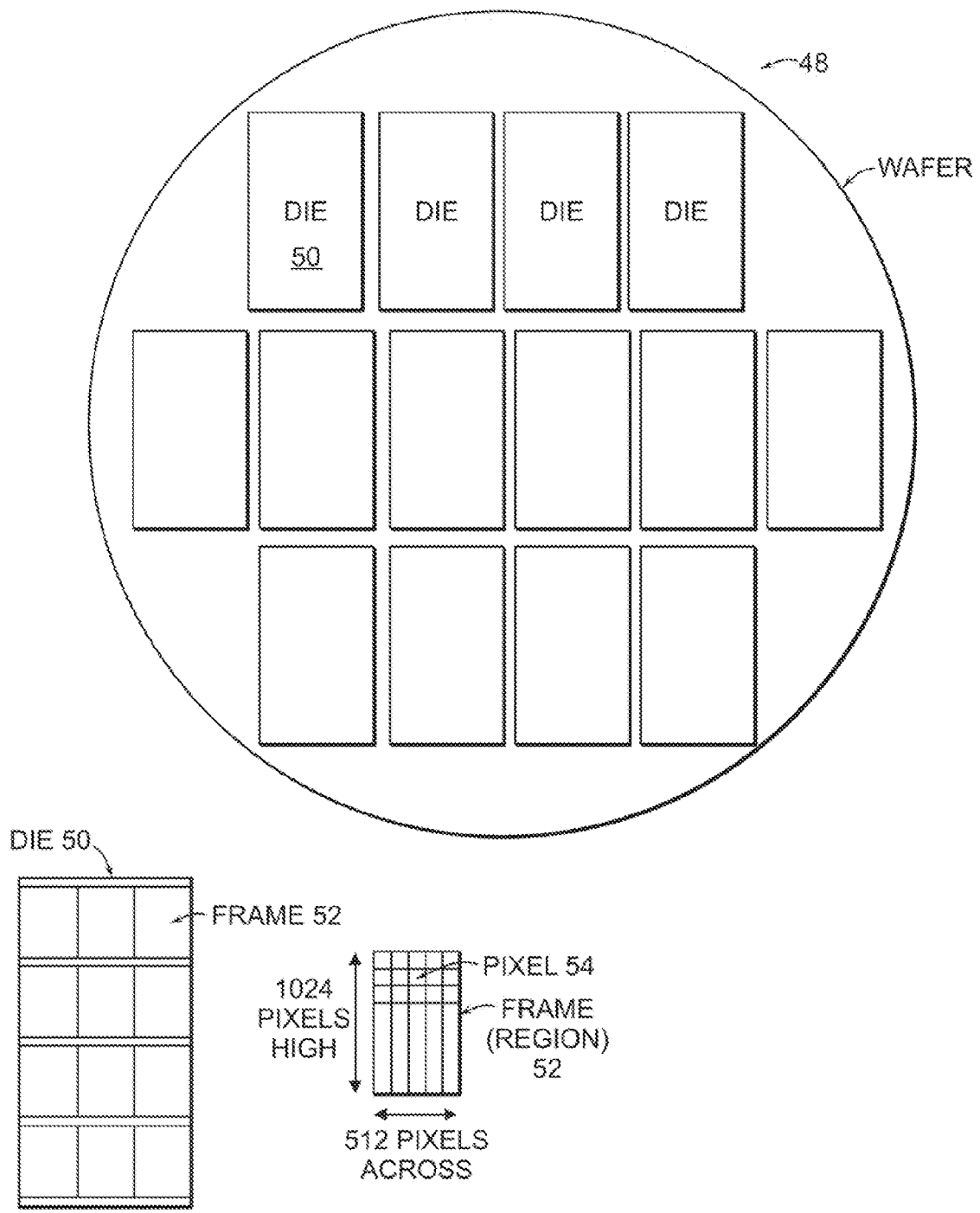
FIG. 4 is a schematic diagram illustrating a top view of one embodiment of a specimen divided into dies, a die divided into frames, and a frame divided into pixels.

In one such example, as shown in FIG. 4, specimen (wafer) 48 includes dies 50. Each die 50 can be broken up into a set of rectangular regions (frames) 52. All of the frames are of the same size. Each frame 52 includes a number of pixels 54. The shape of the frames is, in general rectangular, for example, 512 pixels across×1024 pixels high or square, for example, 512 pixels×512 pixels.

Figure 5:
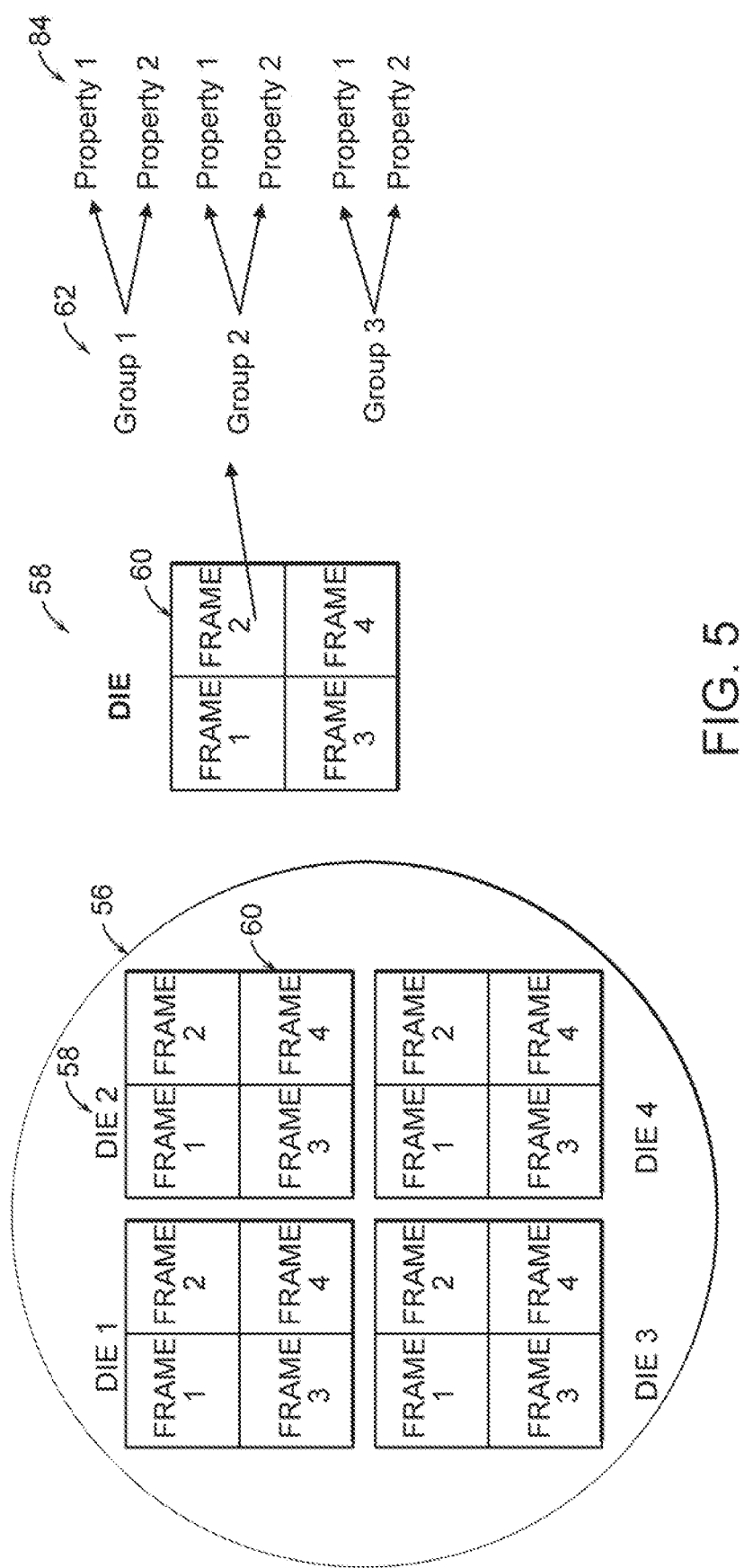
FIG. 5 is a schematic diagram illustrating a top view of one embodiment of a specimen divided into dies, dies divided into frames, a frame divided into groups, and properties determined for each of the groups.

The individual pixels in each region or frame may be further separated into groups based on the output associated with the individual pixels or the property of the individual pixels. For example, as shown in FIG. 5, specimen 56 may include dies 58. Although specimen 56 is shown as including four dies 58, it is to be understood that the specimen may include any suitable number of dies. The specimen may be a wafer. Each of the dies may be divided into frames 60 as described further above. Although each of the dies is shown as being divided into four frames 60, it is to be understood that each of the dies may be divided into any suitable number of frames. As further shown in FIG. 5, the pixels in each of the frames may be separated into groups 62. In addition, although the pixels are shown in FIG. 5 as being separated into three groups, it is to be understood that the pixels in each of the frames may be divided into any suitable number of groups. The pixels may be separated into groups as described further herein.

Individual pixels that appear particularly noisy or appear to contain a large property signal may be separated into one group, and individual pixels that do not appear particularly noisy may be separated into a different group. In this manner, the pixels within each frame can be divided into groups (which may also be referred to as segments), and the pixels belonging to a given group in a given frame need not be adjacent to each other. For example, in each frame, the pixels may be divided into two groups, those whose value (intensity signal) is between 0 and 128 (call this Group 1) and those with values between 128 and 255 (call this Group 2). The Group 1 and Group 2 pixels within a frame can be completely intermixed spatially. In short, a group of pixels within a frame (region) is the collection of pixels that share some common property.

One example of a method that can be used to separate the pixels in such a manner is segmented auto-thresholding (SAT). Generally, SAT is an algorithm that uses pixel-neighborhood statistics to categorize pixels by measuring the noise floor and setting the defect detection threshold higher than that noise floor. Therefore, as the noise floor varies, the threshold "floats." Examples of methods and systems configured for SAT are illustrated in commonly assigned U.S. Pat. No. 6,781,688 to Kren et al., which is incorporated by reference as if fully set forth herein. The method embodiments described herein may include any step(s) of any method(s) described in this patent.

Such a method embodiment may be used to separate individual pixels into groups based on any output associated with the individual pixels or any property of the individual pixels determined as described herein. Obviously, the numbers of pixels that are separated into the different groups may vary in such embodiments, which may result in different numbers of pixels in different groups.

Separating the pixels into groups in the individual regions may also or alternatively be performed based on information about the specimen such as design context associated with the locations of the pixels on the specimen (e.g., such that pixels that are associated with the same design context may be separated into a group) and information about the die layout on the specimen. In this manner, a given pixel in a frame can belong to a given group, which may be defined by either some property or by design context. The term "design context" generally refers to data that defines geometrical areas in a device being formed on the specimen that have different characteristics (e.g., type(s) of features within the areas such as contact areas or dummy fill areas, "where to inspect" information or "care areas," "critical" areas where a process failure is possible, or some combination thereof). The design context associated with the locations of the pixels on the specimen may be determined as described in commonly assigned U.S. patent application Ser. Nos. 11/561,659 by Zafar et al. filed Nov. 20, 2006, 11/561,735 by Kulkarni et al. filed Nov. 20, 2006, 60/868,769 by Fouquet et al. filed Dec. 6, 2006, 60/870,724 by Duffy et al. filed Dec. 19, 2006, 60/883,617 by Park et al. filed Jan. 5, 2007, 11/680,152 by Chen et al. filed Feb. 27, 2007, and 11/683,696 by Chen et al. filed Mar. 8, 2007, all of which are incorporated by reference as if fully set forth herein. The method embodiments described herein may include any step(s) described in these patent applications. For example, the embodiments described herein may include any steps of the design-based methods described in these patent applications. In another example, the embodiments described herein may include any steps of any methods described in these patent applications for recipe setup.

As described above, the property of the individual pixels may be a differential between the properties of the individual pixels located in adjacent dies on the specimen at the same (or substantially the same) within die position. In some embodiments, a portion of the individual regions corresponds to a die on the specimen. For example, as shown in FIG. 3, four of individual regions 44 correspond to die 64 on the specimen. However, the number of individual regions that correspond to a die on the specimen may vary depending on the number of frames per die. In this manner, an entire individual region may correspond to only a portion of a die on the specimen. In other words, the individual regions may include fewer pixels than the die.

In one embodiment, the method includes aligning a portion of the individual regions corresponding to a die on the specimen to a different portion of the individual regions corresponding to a different die on the specimen. For example, the method may include aligning the portion of the individual regions corresponding to die 64 on specimen 42 shown in FIG. 3 to the portion of the individual regions corresponding to die 66 on the specimen. In addition, or alternatively, the method may include aligning the portion of the individual regions corresponding to die 66 to the portion of the individual regions corresponding to die 68. The portions of the individual regions corresponding to different die that are aligned to each other in the method include portions of the individual regions corresponding to different die that are adjacent to one another on the specimen. In this manner, the method may include aligning the corresponding rectangular regions for a selected die to the corresponding rectangular regions for an adjacent die. Aligning the corresponding rectangular regions for multiple dies may be performed using any suitable method and/or algorithm known in the art.

In another embodiment, for each frame, in the case of random inspection, the method may include aligning the frame image of the current die (also called the "test die") to the frame image of the reference die (normally the previous die) and determining the difference image. For example, as shown in FIG. 2, the image of Frame 2 of Die A may be aligned to the image of Frame 2 of Die B, and one of the images may be subtracted from the other image to determine difference image 70. In the case of array inspection, the method may include determining the difference image by using cell-to-cell comparison, which may be performed as described in U.S. Pat. No. 4,845,558 to Tsai et al., which is incorporated by reference as if fully set forth herein.

In another embodiment, the method includes aligning the portion of the individual regions that corresponds to a die on the specimen to a reference die. For example, as shown in FIG. 3, reference die 72 may be stored in database 74. In one such example, the portion of the individual regions corresponding to die 64 on specimen 42 may be aligned to reference die 72. The portion of the individual regions corresponding to die 66 on the specimen may also or alternatively be aligned to reference die 72, and the portion of the individual regions corresponding to die 68 on the specimen may also or alternatively be aligned to reference die 72. The reference die may be, for example, a golden die. In this manner, the method may include aligning the corresponding rectangular regions for a selected die to a golden die. However, the reference die may include any other suitable reference die known in the art. Aligning the corresponding rectangular regions for a die to a golden die may be performed using any suitable method and/or algorithm known in the art.

The golden die may represent a defect free version of the die on the specimen. The golden die may be generated by, for example, inspecting an additional specimen (not shown), identifying a defect free die on the additional specimen, and storing the output generated by inspection of the additional specimen corresponding to the defect free die as the reference die. In another example, the reference die may be generated by simulating the output that would be acquired for a defect free die on the specimen. Simulating the output may include simulating characteristics of a specimen using layout data or design data for the specimen as input to a model of the specimen fabrication process and simulating the inspection of the specimen. Examples of methods and systems that may be used to perform such simulations are illustrated in commonly assigned U.S. patent application Ser. No. 11/226,698 by Verma et al. filed Sep. 14, 2005, published as U.S. Patent Application Publication No. 2006/0062445 on Mar. 23, 2006, which is incorporated by reference as if fully set forth herein. The embodiments described herein may include any other step(s) of any of the method(s) described in this patent application. Database 74 may have any suitable configuration known in the art. In addition, reference die 72 may be stored in database 74 in any suitable format known in the art.

In an additional embodiment, different portions of the individual regions correspond to different dies on the specimen. For example, as shown in FIG. 3, different portions of the individual regions correspond to different dies 64, 66, and 68 on the specimen. In one such embodiment, the method includes aligning the different portions to a common reference grid. In this manner, the method may include aligning rectangular regions corresponding to a collection of dies on the specimen to a common reference grid. Aligning the different portions of the individual regions that correspond to different dies to a common reference grid may be performed using any suitable method and/or algorithm known in the art. The common reference grid may be defined with respect to coordinates of the specimen, the die, or any other suitable coordinate system.

In summary, therefore, the properties of the individual pixels can be any function of the gray level (signal) at a given pixel, a function of the neighborhood of pixels around the pixel, the difference between the function value at the pixel and the function value at the corresponding pixel location in an adjacent die or any reference die or golden die, or some combination thereof.

Figure 6:
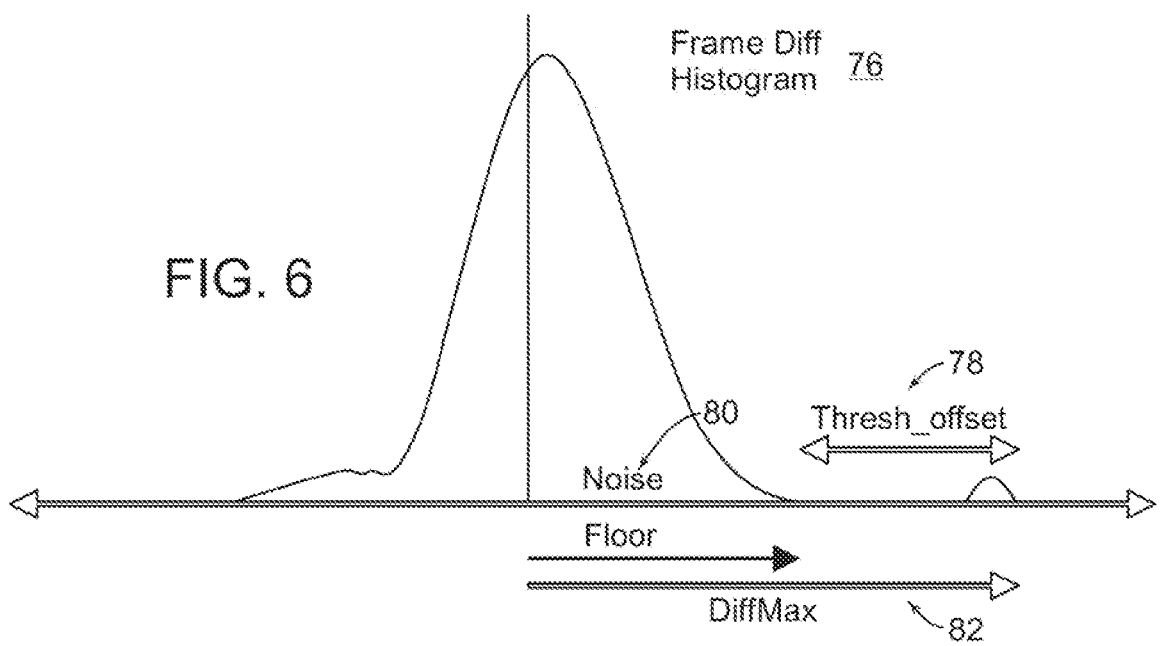
FIG. 6 is schematic diagram illustrating one embodiment of a histogram determined by an auto-threshold algorithm.

The method also includes determining a characteristic of the individual regions using the properties of the individual pixels in the individual regions. For example, any properties that can be extracted from the original frame image or the difference image can constitute the frame data. One possible property includes any statistics of the pixel values of the frame image, such as average, standard deviation, median, minimum, maximum, or percentile. Another possible property includes any statistics of the pixel values of the difference image, such as average, standard deviation, median, minimum, maximum, or percentile. An additional possible property includes any intermediate results determined by the detection algorithm. For example, in the case of an auto-threshold algorithm, the algorithm determines a histogram of the difference image and uses it to automatically determine a threshold for detecting defective pixels. The properties that can be extracted from this detection algorithm include the target density position, the extreme pixel value, and the offset. For example, as shown in FIG. 6, the algorithm may determine frame difference histogram 76, and the properties that can be extracted from this detection algorithm include threshold offset 78, noise floor 80, and maximum difference 82.

If the recipe contains multiple regions, and there is more than one region in a frame, then the above-mentioned frame data is collected for each region. In other words, the steps of frame data extraction are applied to all the pixels belonging to each region.

To reduce the file size when saving, the frame data may be compressed. The compression scheme may be tailored for the type of frame data collected.

The compressed frame data may be written to the file with auxiliary information that enables the construction of wafer and die images as described further herein. This auxiliary information includes the swath indices, die indices, and frame indices, and other parameters related to swath and frame layout. The compressed frame data is written to and subsequently appended to a file at a time. When the inspection is completed, the file is closed and saved to disk.

In one embodiment, the properties of the individual pixels used to determine the characteristic of each of the individual regions include the properties of all of the individual pixels within each of the individual regions. In this manner, the region characteristic may be any statistic of a pixel property measured over all of the pixels within the region (frame). Alternatively, the properties of the individual pixels used to determine the characteristic of the individual regions include the properties of only a portion of the individual pixels within each of the individual regions. The properties of the individual pixels that are used to determine the characteristic of the individual regions may be selected based on, for example, the values of the properties and the characteristic of the individual regions that is being determined.

The method may also include determining a characteristic of different groups of pixels in each of the regions or frames. For example, as shown in FIG. 5, the pixels in one of frames 60 may be separated into three groups 62 (e.g., Group 1, Group 2, and Group 3). One or more properties for each of the groups may be determined. For example, as shown in FIG. 5, properties 84 (e.g., Property 1 and Property 2) may be determined for each of the groups of pixels. The properties of the different groups of pixels may be determined as described further herein. In addition, as shown in FIG. 5, both Property 1 and Property 2 may be determined for each of the groups of pixels. The property or properties that are determined for each of the groups of pixels may be the same property or properties.

In one embodiment, the characteristic of the individual regions includes a statistic of the properties of the individual pixels within the individual regions. The statistic may include any of the statistics described herein or any other appropriate statistic. In an additional embodiment, the characteristic of the individual regions includes a distribution of the properties of the individual pixels within the individual regions. For example, determining the property of the individual pixels as described above may include determining a property of each pixel location within each individual region, and determining the characteristic of the individual regions may include determining a distribution of that property for the pixels in each region (e.g., a histogram of pixel count versus the property value). In some embodiments, as described above, the property of the individual pixels is a differential between the properties of the individual pixels located in adjacent dies on the specimen at the same (or substantially the same) within die position. In one such embodiment, the characteristic of the individual regions includes a distribution of the differentials of the individual pixels within the individual regions. In this manner, determining the characteristic of the individual regions may include determining a distribution of the property of the individual pixels in each region (e.g., a histogram of this difference value).

In a further embodiment, the characteristic of the individual regions includes a property of a distribution of the properties of the individual pixels within the individual regions. For example, determining the characteristic of the individual regions may include determining (and optionally recording in some manner) some value of a distribution of the properties of the individual pixels within the individual regions (e.g., a histogram of the signal value, a histogram of the difference between the signal values from adjacent dies, one or more histograms of one or more statistics for pixels at corresponding die-relative locations in two or more dies in a die row (e.g., all of the die in a die row), etc.). The property of the distribution may be, for example, the highest value recorded in the rectangular region such as the maximum signal value or the maximum difference of signal values (between adjacent dies), a measure of the spread of the distribution such as standard deviation, or the average value of the distribution or the mode (e.g., location of the peak in the histogram). In yet another embodiment, the characteristic of the individual regions includes a property of a distribution of the properties of the individual pixels within the individual regions and a location corresponding to the property of the distribution. For example, determining the characteristic of the individual regions may include determining (and optionally recording in some manner) the x and y location of the pixel exhibiting, for example, the maximum signal in the distribution (e.g., histogram). Thus, if the histogram is determined for the gray level difference between adjacent dies on the specimen, the location may be that of the pixel exhibiting the largest difference value.

In some embodiments, determining the characteristic of the individual regions includes separating the individual pixels into groups based on design context associated with the individual pixels. In this manner, the pixels in the individual regions may be separated according to design context. Such separation of the pixels into groups may be performed as described above. In one such embodiment, the characteristic of the individual regions includes a characteristic of the groups. The characteristic of the groups that is determined in this embodiment may include any of the characteristics of the individual regions described herein and may be determined as described herein.

As also described above, the individual pixels in the individual regions may be separated into groups based on the property of the individual pixels. Regardless of how the individual pixels are separated into groups, a characteristic can be determined for each or one or more of the groups in a manner similar to that described above with respect to determining a characteristic of the individual regions. In addition, more than one characteristic can be determined for each or one or more of the groups as described above. For example, the group characteristic (a group property or region (frame) property) may include a statistic of a pixel property measured over all of the pixels in the group or region (frame). The characteristic(s) of the groups may include any of the characteristic(s) described herein.

In summary, therefore, the characteristic of the individual regions or the characteristic of the groups may be an average gray level of pixels, an average die-to-die difference of gray levels, standard deviation of gray level difference between pixels in adjacent dies belonging to that region (frame) or group, or some combination thereof.

The method also includes monitoring the characteristic of the specimen based on the characteristics of the individual regions. In some embodiments, the characteristic of the specimen includes a specimen-level signature in the characteristics of the individual regions. In another embodiment, the characteristic of the specimen includes a die-level signature in the characteristics of the individual regions. The signatures described above may be "systematic property signatures" extracted from a specimen property map.

The specimen property map may be generated by dividing a die swath into frames (e.g., 512×512). A frame in one die can then be sub-pixel aligned with a corresponding frame in another die. The frame pixels may be grouped into "SAT segments" automatically based on, for example, gray level and local range. There may be K segments, typically 3-8. A histogram of the gray level difference for the $i^{th}$ segment pixels between two die may then be determined. Statistics of this difference histogram for each segment and for each pair of consecutive dies may be recorded. The statistic may include statistics such as pixels in the segment, maximum gray level difference, and location (gray level value) in the histogram tail of the bottom p % of pixels (e.g., 0.001%, 0.01%, 0.1%, etc.) (no location information may be recorded for where the pixels in the histogram tail lie, only defect locations may be recorded).

The specimen property map may illustrate the distribution of segment populations across a die, specimen scale changes in the population distributions, distribution of die-to-adjacent die property distribution in a die, specimen scale changes in the property distribution, and distinct signatures that correspond to system level problems. For example, distinct signatures may be identified in different SAT segments that indicate specimen-scale issues that are likely important.

The specimen-level and/or die-level signatures may be determined by spatial signature analysis (SSA) of a characteristic of the individual regions such as the property map across one or more of the individual regions. In this manner, the specimen-level and/or die-level signatures may be detected using a type of image analysis. Examples of SSA methods and systems that may be used in the embodiments described herein are illustrated in commonly assigned U.S. Pat. Nos. 5,991,699 to Kulkarni et al., 6,718,526 to Eldredge et al., and 7,006,886 to Huet et al., which are incorporated by reference as if fully set forth herein. The embodiments described herein may include any step(s) of any of the method (s) described in these patents.

In this manner, the method embodiments may include determining specimen-level and/or die-level signatures in output generated by inspecting the specimen. Such output may be generated by currently available inspection systems such as the AIT, 23xx, and eS30 family of tools that are commercially available from KLA-Tencor. However, output generated by such tools is currently discarded after the output is determined to not indicate defects on the specimen (e.g., the output signals are below the threshold value used to identify defects on the specimen).

The method may also include generation of wafer and die signature images. For example, for each property of frame data collected in a frame, a separate signature wafer or die image can be generated. In one embodiment, the method includes constructing a signature image of the specimen, and each pixel of the signature image represents a selected characteristic of the individual regions. For example, to generate a wafer signature image, the selected property of each frame is read from the frame data, and converted to a pixel value. The pixel position of this frame is determined from the auxiliary data mentioned above. To construct the die signature image, the wafer images are split into die according to the die size and location information. The tool then determines the minimum of the stack of die images to obtain the die signature image.

Figure 7:
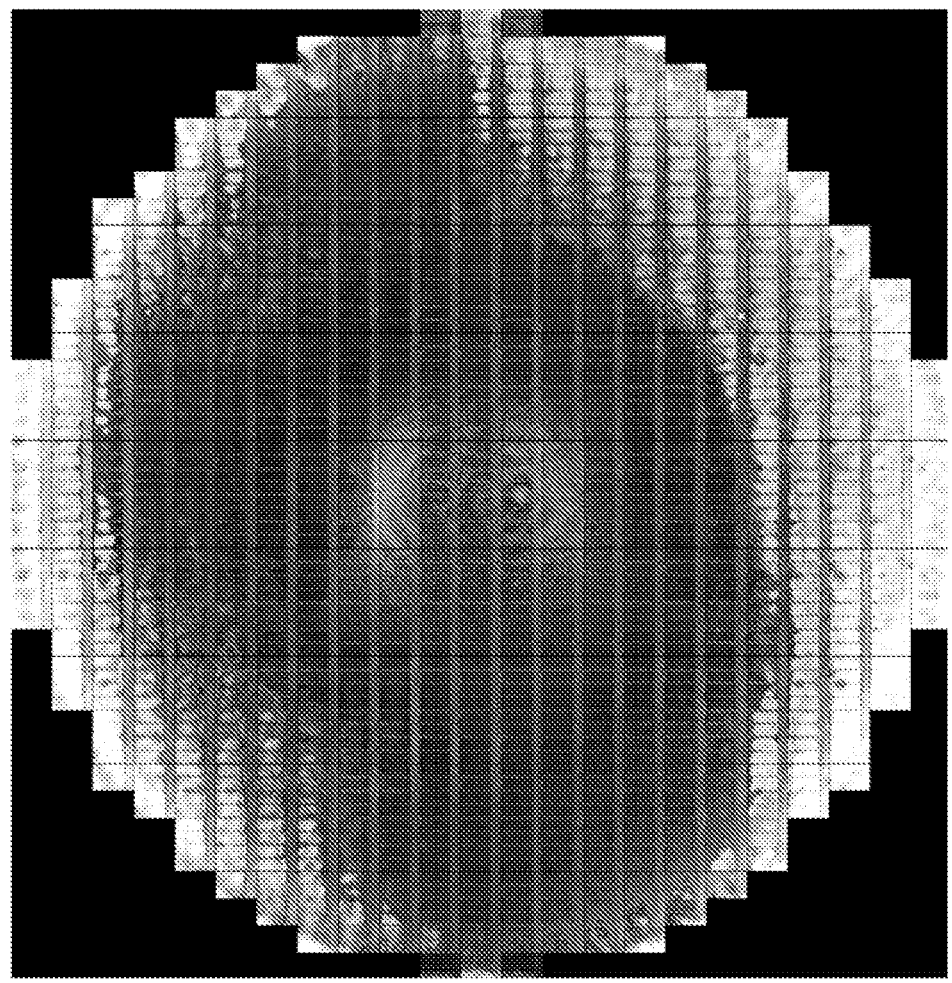
FIG. 7 is a schematic diagram illustrating one embodiment of a wafer signature image generated in gray scale.

The method may also include visualization of wafer and die signature images. For example, for visualization, the tool may provide a user interface (UT) for users to select any one of the properties collected in the frame data. The tool displays the corresponding wafer signature images generated as described above in gray scale (e.g., as shown in FIG. 7, which includes an example of a wafer signature image) or in some suitable color map. To make the signature more visual to human eyes, the system may automatically adjust the contrast of certain range(s) of the signature image. In one embodiment, the method includes displaying two or more signature images side by side In another embodiment, the method includes displaying one or more signature images overlaid on a wafer map of defects. For example, to facilitate the mapping of the detected defects to the wafer signatures, the wafer map of defects and the wafer signature image are displayed side-by-side, or overlaid, with the die signature map.

In the embodiments described herein, signatures in such output can be used to monitor wafer defectivity and metrology issues. These signatures usually correspond to systematic issues that cannot be detected by metrology or "parametric" measurements because of throughput concerns (sampling). In particular, metrology measurements are point-to-point measurements. In other words, the measurements are performed at one location on the specimen while the specimen is stationary, then the specimen is moved such that the measurements can be performed at a different location on the specimen. Therefore, due to the low throughput of metrology tools compared to that of inspection systems, it is impractical to perform metrology measurements across an entire specimen. However, the embodiments described herein utilize output generated by an inspection system. Therefore, the output that is used in the embodiments described herein to monitor for such systematic issues can be generated relatively quickly.

The systematic issues that can be identified and analyzed in the embodiments described herein include any systematic issues known in the art. Furthermore, because the embodiments described herein can be used to identify and analyze systematic issues across an entire specimen in a relatively short amount of time, the embodiments described herein may be particularly useful for applications in which a substantial amount of learning is desired. For instance, the introduction of new technologies such as immersion lithography to fabrication processes may cause new types of defectivity on the specimen. Due to the relatively large number of variable parameters of the fabrication processes and the substantial differences between new and old technology (e.g., between non-immersion and immersion lithography), the new types of defectivity may be difficult to predict and control. However, the embodiments described herein can generate a substantial amount of information about defectivity across an entire specimen in a relatively short amount of time, which provides effective and cost efficient methods and systems for identifying and eliminating new types of defects thereby reducing the time-to-market and increasing the profitability of the fabrication processes.

The characteristics of the individual regions such as the region statistics described above may, therefore, be used to monitor some basic issues on the specimen. For example, a template such as that used for SAT may be configured to detect color variation by choosing a segment with a low range and medium to high mean. Color variation usually tracks with film thickness variation so in principle parametric measurements can be correlated with these measurements, and this data may be included as part of the inspection results for the specimen. In another example, the maximum difference per SAT segment, other segment-based statistical properties, absolute measures like brightest pixel per frame and darkest pixel per frame, or some combination thereof may be tracked. In addition, the characteristics of the individual regions that are used to monitor the characteristic of the specimen in the embodiments described herein may be determined as described in commonly assigned U.S. Pat. No. 6,781,688 to Kren et al., which is incorporated by reference as if fully set forth herein. The method embodiments described herein may include any step(s) of any of the method(s) described therein. Other automatic thresholding algorithms (e.g., the HLAT algorithm) may be used in a similar manner in the embodiments described herein.

In some embodiments, the method includes determining potential process problems based on the characteristics of the individual regions and generating output illustrating the potential process problems. For example, as described above, the output generated by an inspection system is used to determine the characteristics of the individual regions, and the characteristics of the individual regions such as color variation can be used to determine a potential process problem such as an improperly functioning lithography track (e.g., an improperly functioning resist apply module). In this manner, the embodiments described herein may include specimen property analysis and systematic process issues. The systematic process issues that may be detected in the embodiments described herein include, but are not limited to, critical dimension (CD) variation, film thickness variation, line edge roughness, and etch depth. For example, the characteristic of the individual regions that is determined in the embodiments described herein may include a pattern property that may be directly correlated to CD variation. The characteristics of the individual regions may be correlated to potential process problems in any manner known in the art (e.g., a priori or based on experimentation). In addition, the potential process problems may be determined from the characteristics of the individual regions using any suitable method, algorithm, and/or data structure known in the art (e.g., a database, a rules database, a look up table, a functional relationship, etc.). The output illustrating the potential process problems may include concurrent multiple specimen-level and die-level views showing the potential process problems. The views may also include views showing the potential process problems across specimen by die or across specimen-to-specimen. The output illustrating the potential process problems may have any suitable format known in the art.

In some embodiments, the characteristic of the specimen determined from the one or more characteristics of individual regions or groups on the specimen may include a table showing the value of each characteristic determined for each region (frame) of each die or for each group in each region of each die. In other words, the table may illustrate the determined characteristic(s) as a function of region and die or as a function of group, region, and die. Table 1 below illustrates one example of such a table.

TABLE 1

|  | Group 1 | | Group 2 | | Group 3 | |
| --- | --- | --- | --- | --- | --- | --- |
|  | Property 1 | Property 2 | Property 1 | Property 2 | Property 1 | Property 2 |
| Die 1 Frame 1 | 26 | 57 | 30 | 94 | 23 | 108 |
| Die 1 Frame 2 | 05 | 90 | 08 | 94 | 10 | 240 |
| Die 1 Frame 3 | 125 | 57 | 148 | 22 | 110 | 108 |
| Die 1 Frame 4 | 75 | 57 | 64 | 94 | 70 | 108 |
| Die 2 Frame 1 | 26 | 57 | 30 | 94 | 23 | 108 |
| Die 2 Frame 2 | 26 | 57 | 30 | 94 | 23 | 108 |
| Die 2 Frame 3 | 26 | 57 | 110 | 94 | 23 | 200 |
| Die 2 Frame 4 | 26 | 88 | 30 | 94 | 23 | 108 |
| Die 3 Frame 1 | 26 | 57 | 30 | 94 | 23 | 108 |
| Die 3 Frame 2 | 26 | 57 | 30 | 94 | 23 | 155 |
| Die 3 Frame 3 | 26 | 11 | 120 | 94 | 23 | 108 |
| Die 3 Frame 4 | 26 | 57 | 30 | 94 | 44 | 108 |
| Die 4 Frame 1 | 26 | 57 | 30 | 94 | 23 | 111 |
| Die 4 Frame 2 | 99 | 05 | 30 | 94 | 66 | 220 |
| Die 4 Frame 3 | 26 | 57 | 130 | 94 | 23 | 139 |
| Die 4 Frame 4 | 26 | 20 | 30 | 94 | 23 | 108 |

Figure 8:
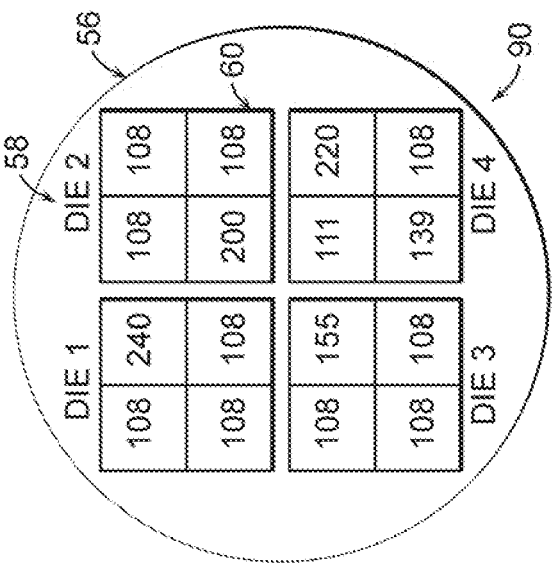
FIG. 8 is a schematic diagram illustrating examples of group property maps.
Figure 8:
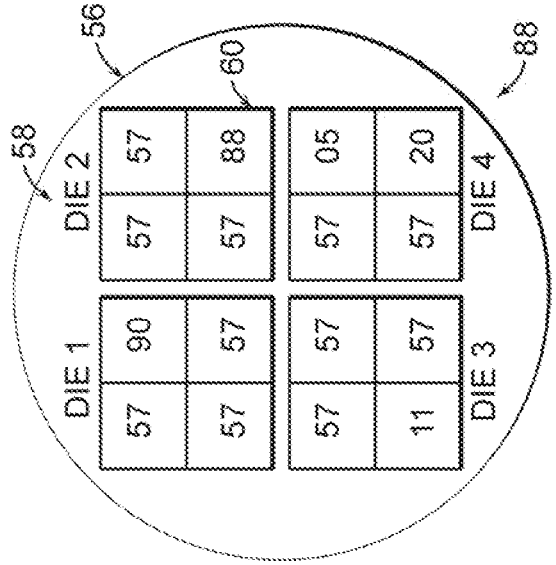
Figure 8:
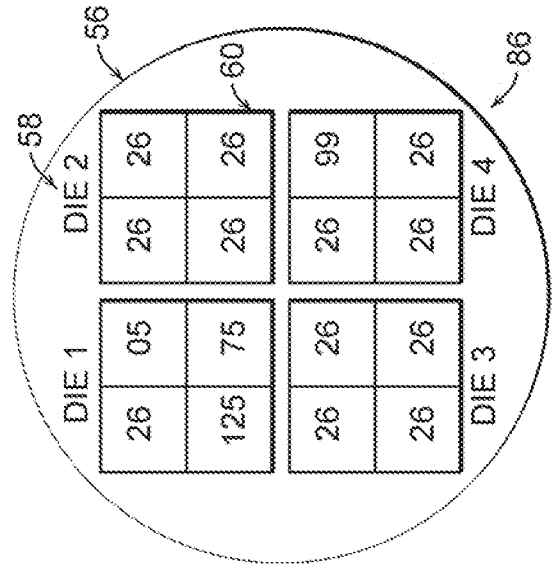

In another embodiment, the characteristic of the specimen determined from the one or more characteristics of individual regions or groups on the specimen may include one or more maps, each of which shows the value of one characteristic as a function of region (frame) and die or as a function of group, region, and die. Alternatively, each of the one or more maps may show the value of only one characteristic for only one type of group per region (frame) in one or more dies on the specimen. For example, one map may illustrate the values of a first characteristic for only a first type of group in each region in more than one die on the specimen, another map may illustrate the values of the first characteristic for only a second type of group in each of the regions in more than one die on the specimen, and an additional map may illustrate the values of a second characteristic for only a third type of group in each of the regions in more than one die on the specimen. Examples of such group property maps are shown in FIG. 8. In particular, group property map 86 illustrates Property 1 for Group 1 for each of frames 60 in dies 58 formed on specimen 56. Group property map 88 illustrates Property 2 for Group 1 for each of frames 60 in dies 58 formed on specimen 56. Group property map 90 illustrates Property 2 for Group 3 for each of frames 60 in dies 58 formed on specimen 56. In this manner, each map may illustrate the values of only one characteristic of only one type of group of individual pixels as a function of region and die on the specimen.

In one embodiment, the method includes identifying one or more of the individual regions having unique characteristics. For example, the method may include identifying the individual region(s) having the largest pattern property variation or the individual region(s) having the largest color variation. Unique characteristic(s) may be defined on a characteristic-to-characteristic basis. For example, the lowest value of some characteristics may be unique while for other characteristics, the highest value may be unique. The individual regions may be identified as having unique characteristics in any suitable manner (e.g., comparing the characteristic of each region to the characteristics of each of the other regions or comparing the characteristic of each region to some predetermined criteria that defines the values of the characteristic that are to be considered unique, which may be defined by the user or automatically by the methods described herein).

Figure 9:
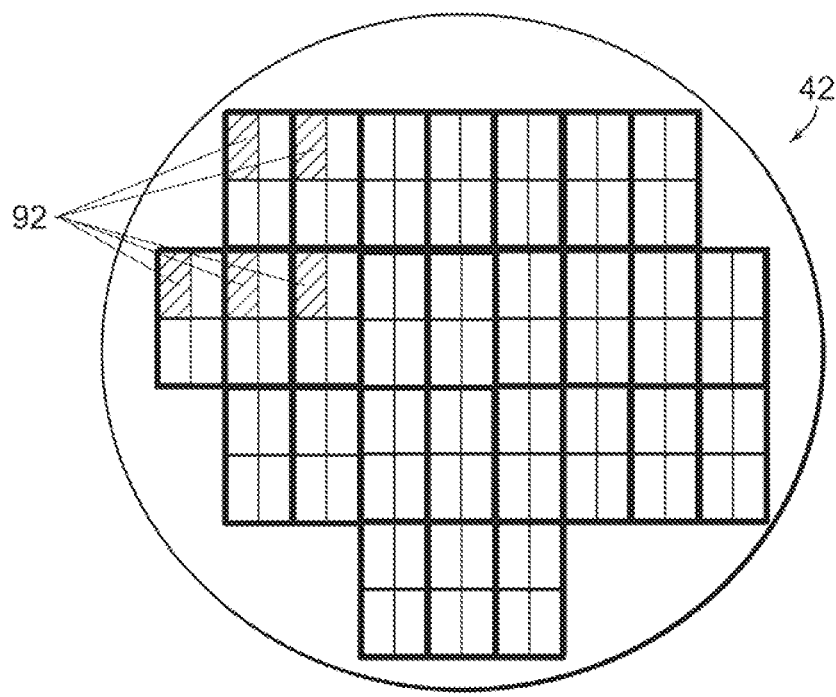
FIG. 9 is a schematic diagram illustrating a top view of one embodiment of individual regions on a specimen identified as having unique characteristics.

In one such embodiment, as shown in FIG. 9, individual regions 92 may be identified as individual regions of specimen 42 that have unique characteristics. Although a certain number of individual regions 92 having unique characteristics are shown in FIG. 9, it is to be understood that any number of individual regions (e.g., one or more) may be identified as having unique characteristics. In addition, although individual regions 92 are shown as having particular locations on specimen 42, it is to be understood that the individual regions identified as having unique characteristics may be located in any position on the specimen.

In another embodiment, the method includes selecting one or more of the individual regions having unique characteristics for metrology. The one or more individual regions that are selected for metrology may include all or some of the individual regions that are identified as described above. In addition, the metrology that is performed on the individual regions may include any suitable metrology known in the art and may vary depending on, for example, characteristics of the specimen and/or the process(es) previously performed on the specimen. Other analysis processes such as defect review and/or defect or material analysis may also be performed on the regions selected for metrology.

In a further embodiment, the method includes determining one or more locations on the specimen corresponding to one or more of the individual regions having unique characteristics and generating information about the one or more locations that can be used to perform one or more measurements at the one or more locations. In this manner, the embodiments described herein may be used to lead a metrology tool or a user to exact spots on a specimen where specimen-level and/or die-level issues are unique (e.g., the worst). The one or more locations on the specimen corresponding to the individual region(s) having unique characteristics may be determined in any suitable manner (e.g., from positional information generated by the inspection system). In addition, the individual region(s) for which location(s) are determined may include, for example, all of the individual region(s) identified as having unique characteristics or only those individual region(s) selected for metrology.

The one or more measurements that are to be performed on the one or more individual regions may include any suitable metrology measurement(s) known in the art including those described herein. In addition, the one or more measurements may be performed by a single metrology tool or by more than one metrology tool. For example, the one or more measurements may include two or more different types of measurements that are performed by a single metrology tool or multiple metrology tools.

The information generated about the one or more locations that can be used to perform the one or more measurements may vary depending on the measurement(s) to be performed on the individual region(s). For example, if the metrology tool that will perform the measurement(s) can determine the locations of the individual regions on the specimen from output generated by the inspection system, the information may include a subset of all of the location information generated by the inspection system corresponding to the one or more individual regions for which measurements are to be performed. Alternatively, the format of the information may be a standard file format or a format that can be used by the metrology tool without conversion of the information. For example, generating the information can include transforming the coordinates of the individual region(s) at which the measurement(s) are to be performed as reported by the inspection system to coordinates of the individual region(s) with respect to the metrology tool(s). In another example, the information may be in the form of a standard file format that is readable and usable by a number of tools (e.g., both inspection and metrology tools). One example of such a standard file format is the KLARF file format.

In another embodiment, the characteristic of the specimen includes the characteristic of the individual regions as a function of position across the specimen. In one such embodiment, monitoring the characteristic of the specimen includes determining similarities between the characteristic of the specimen and a reference. For example, the method may include comparing a specimen map of the characteristic of the specimen or the characteristics of the individual regions to a stored database of specimen maps in order to determine similarities between such maps. The similarity measure may be, for example, a direct matching between the values of the maps (such as a correlation function) or a similarity between feature vectors extracted from the maps. A feature vector may be determined for any set of properties of the specimen map. This step can be viewed as classification of the specimen map into one of a set of predetermined categories or classes (e.g., a normal map versus an abnormal map).

In an additional embodiment, monitoring the characteristic of the specimen includes monitoring the characteristic of the specimen on a specimen-to-specimen basis or a lot-to-lot basis by comparing the characteristic of the specimen to one or more control limits. For example, monitoring the characteristic of the specimen may include tracking from specimen-to-specimen or lot-to-lot some characteristic of the specimen and triggering an alarm when that characteristic violates some control limits. The one or more control limits may be selected in any manner known in the art and can have any suitable format known in the art. The alarm may have any suitable format known in the art. In this manner, the method may include statistical process control (SPC) by monitoring a characteristic of the specimen based on output generated by inspection of the specimen.

In some embodiments, monitoring the characteristic of the specimen includes comparing the characteristic of the specimen to one or more control limits and determining locations on the specimen at which the characteristic of the specimen exceeds the one or more control limits. The characteristic of the specimen that is compared to the one or more control limits may include any of the characteristics of the specimen described herein. The one or more control limits may be selected in any manner known in the art and can have any suitable format known in the art. The locations on the specimen may be determined based on location information about the individual regions, dies, and/or individual pixels on the specimen. In other words, the locations on the specimen at which the characteristic of the specimen exceeds the one or more control limits may be determined using any positional information generated by the inspection system or generated by the embodiments described herein.

In one such embodiment, the method also includes generating information about the locations that can be used to perform one or more measurements at the locations. The information about the locations can include any of the information described above. In this manner, the method may include recording specimen locations at which the chosen characteristic exceeds the control limit(s) so that those specimen locations can be measured using a metrology tool, for example, to measure line widths with high precision, to examine manually using a high-resolution review microscope such as an optical microscope or an electron beam microscope, or any of the other metrology measurements described herein.

Figure 10:
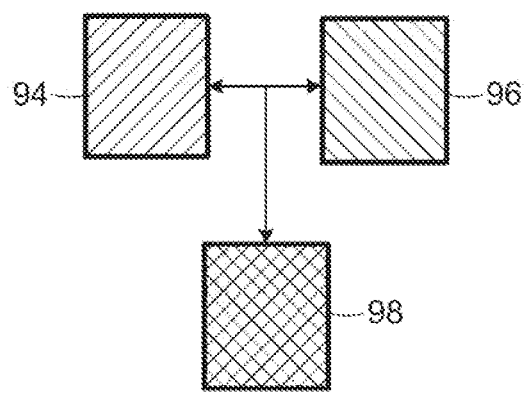
FIG. 10 is a schematic diagram illustrating a top view of one embodiment of characteristics of an individual region on a specimen corresponding to at least one die on the specimen combined with characteristics of another individual region on the specimen corresponding to at least one additional die on the specimen.

In some embodiments, the characteristic of the specimen includes the characteristics of the individual regions corresponding to at least one die on the specimen combined with the characteristics of the individual regions corresponding to at least one additional die on the specimen. For example, determining the characteristic of the specimen may include "stacking" two or more individual dies on the specimen and displaying a stacked die map. In other words, the characteristics of individual regions corresponding to two or more die on the specimen may be overlaid. In one such example, characteristics of die 94 shown in FIG. 10 on a specimen (not shown in FIG. 10) may be overlaid with characteristics of die 96 on the specimen to produce combined characteristics of the two die shown as stacked die map 98.

The die that are stacked can be chosen by a user of the embodiments described herein or selected automatically using some algorithm and/or method. The values of the characteristics of the individual region(s) corresponding to multiple dies can be combined in any number of ways (e.g., average value, median value, minimum or maximum value, etc.). For a binary specimen map, die stacking may be performed using a Boolean function of all of the individual binary values of individual region(s) corresponding to the multiple dies. The Boolean function may be, for example, a union or intersection function or a count function in which the number of values with a binary value equal to one at that location could be counted. The method may also include displaying the stacked die map as either a binary image (using some threshold value) or an image in which the characteristics are displayed as a gray level value or as a color-coded value for easy viewing by a user of the embodiments.

In one such embodiment, monitoring the characteristic of the specimen includes determining similarities between the combined characteristics and a reference. For example, such monitoring of the characteristic may include comparing a stacked die map of a specimen to a stored database of stacked die maps in order to determine similarities between such maps. The similarity measure may be a direct matching between the values of the maps (such as a correlation function) or a similarity between feature vectors extracted from the maps. A feature vector may be determined for any set of properties of the stacked die map. This step can be viewed as classification of the stacked die map into one of a set of predetermined categories or classes (e.g., a normal map versus an abnormal map). In another example, such monitoring of the characteristic may include tracking from specimen-to-specimen or lot-to-lot some property of the stacked die map and triggering an alarm when that property violates some control limits. Such tracking and triggering of the alarm may be performed as described herein.

In a further embodiment, the method includes detecting defects on the specimen using the output while monitoring the characteristic of the specimen. The defects may include any type of defects known in the art and may vary depending on the type of specimen being inspected. Detecting the defects may be performed using any suitable method and/or algorithm known in the art. In this manner, the specimen may be inspected by an inspection system and defects may be detected as before, but at the same time a characteristic of the specimen may also be monitored. As such, the methods described herein can perform defect detection while monitoring the specimen for other systematic issues. In particular, the embodiments described herein can be used to find systematic process issues and defects simultaneously using defect inspectors in parallel with micro-defect detection. For example, as the specimen is scanned during inspection, defect detection may be performed at the pixel level while also determining a characteristic (e.g., a statistic) of the individual regions (e.g., frames) on the specimen and performing analysis as described herein. In one such example, the output generated by the inspection system may be compared to a threshold to detect defects on the specimen thereby identifying defect signals in the output. The output can then be used in the embodiments described herein. In addition, a defect map illustrating the locations of detected defects on the specimen may be generated. The defect map may be overlaid on a map illustrating the characteristics of the individual regions on the specimen to determine whether the detected defects are isolated or are part of a larger defect population.

In another embodiment, the method includes generating output illustrating the property of each of the individual pixels corresponding to one of the individual regions as a function of position across the one individual region. In this manner, the method may include generating a region-level view of the properties of the individual pixels corresponding to the region. The output may include any suitable output such as a two-dimensional map of the property of each of the individual pixels corresponding to the individual region. The method may also or alternatively include generating such output as a function of position across the specimen. For example, the embodiments may include displaying the value of the property on a two-dimensional display surface (e.g., a graphical user interface (GUI)) by encoding the value as a gray level or color encoded for easy viewing by a human. In one such example, the output may be a specimen map of the property in which each pixel value in the display shows the value of that property in a given rectangular region within a die. In this manner, the output may be an image of the property of individual pixels across a region or across the specimen. In one such example, the property of the individual pixels may be a property value of the individual pixels. Therefore, the image may be an image of the property measured across a region or across a specimen. Examples of methods and systems for generating such images are illustrated in commonly assigned U.S. patent application Ser. No. 11/673,150 by Kirk et al. filed Feb. 9, 2007, which is incorporated by reference as if fully set forth herein. The embodiments described herein may include any other step(s) of any method(s) described in this patent application. Such an image may be used to monitor a characteristic of the specimen as described herein.

According to an additional embodiment, the method includes comparing the properties of the individual pixels to a threshold value and generating output indicating the individual pixels on the specimen having a property that is above the threshold value and the individual pixels on the specimen having a property that is below the threshold value. The threshold value may include any suitable threshold value known in the art. Obviously, the threshold value will vary depending on the property. The threshold value may be selected by a user of the embodiments described herein or may be selected by the embodiments described herein. The output may be generated in any manner known in the art. In addition, the output may have any suitable format such as a two-dimensional map of an individual region, an individual die, or the specimen. The two-dimensional map may separately indicate individual pixels having values above and below the threshold. In one such example, the output may include a display of a binary version of the specimen map based on a threshold value such that all pixels in the display with values less than the threshold are black and those above are white or vice versa.

In some embodiments, the method includes determining if the properties of the individual pixels within two or more die on the specimen are correlated. In this manner, the method may include determining if property measures within a die are highly correlated. In another embodiment, the method includes identifying portions of two or more die on the specimen in which the properties of the individual pixels are correlated as locations of a potential systematic defect causing mechanism on the specimen. Such a method may also include displaying highly correlated die regions (e.g., frames) to the user as being possible sites at which some systematic defect causing mechanism may be at work.

Such systematic events may be detected by measuring the correlation between "peak property events" at corresponding locations in multiple dies. This embodiment of the method may be regarded as an extension of a "repeater analysis" method in which defects occurring at the same (or substantially the same) die-relative location in many dies are flagged as repeater defects. Examples of such methods are described in commonly assigned U.S. patent application Ser. Nos. 11/561,659 by Zafar et al. filed Nov. 20, 2006 and 11/561,735 by Kulkarni et al. filed Nov. 20, 2006, both of which are incorporated by reference as if fully set forth herein.

Die-to-die or die-to-golden die defect detection methods involve comparing aligned images of two die, one of which is commonly referred to as the "target die," the other of which is commonly referred to as the "reference die," to identify and flag defective pixels. Generally, defective pixels are those whose die-to-reference die gray level difference exceeds some threshold value. However, often, some systematic defect causing mechanism may cause certain locations within the die to behave similarly to process variations and while the gray level values at these locations may not cause them to be flagged as defects, it may be useful to know that these locations are varying in a correlated fashion and could (if the process deteriorates further) cause defects to occur at these spots.

Thus, by examining the correlation of die-to-die pixel differences, it may be possible to detect systematic difference trends within the die. There is a strong possibility that such systematic difference trends in certain locations within the dies may be due to a systematic defect mechanism at work at these locations which share a common design context. For example, some geometries in a design are more susceptible to systematic defects than others. Therefore, pixel properties at the locations of similar geometries may indicate that a systematic defect mechanism is occurring in these geometries. In contrast, variations in characteristics at the locations of similar geometries may indicate that the geometries are not susceptible to systematic defect mechanisms. In this manner, the method embodiments described herein may use correlation analysis to detect systematic defects.

An exhaustive method for examining such gray level difference correlations is to measure the cross-correlation of all pixel pairs in the die image across all dies on a specimen. However, even to study a second-order correlation (i.e., a correlation between two pixels), one would have to compute a cross correlation matrix of size $N^2*N^2$ for an N×N image and look for pixel pairs with a high cross-correlation value. For higher order correlations, for example, for examining all triplets of pixels that are correlated, the combinatorial explosion makes the computation impractical.

Correlation analysis may alternatively be performed using peak event correlation to keep the computation load within practical limits. This method utilizes the concept of "peak property events" (i.e., the locations of pixels at which the die-to-die difference values exceed a threshold value). The peak events detected at a given threshold value, T, are analyzed across all dies on a specimen to measure their correlation. Assume that there are M die on the specimen. The correlation between two peak events, denoted by $p_i$ and $p_j$ is measured by the quantity, $Corr[p_i, p_j] = \#(p_i, p_j)/\{\#p_i * \#p_j\}^{1/2}$ where Corr[ ] denotes the correlation between two events, $\#p_i$, $\#p_j$ denote the number of occurrences of the events $p_i$ and $p_j$, respectively, in all of the dies on the specimen, and $\#(p_i, p_j)$ denotes the number of die in which both events occur together. An event $p_i$ is uniquely identified by its die-relative location (i.e., its (x, y) location within the die). Corr[ ] will have a value between 0 and 1, where 1 denotes that both events always occur together.

If there are an average of n(T) peak events per die at a threshold value=T, then the number of pair-wise event correlations computed is n(T)*n(T)/2. This number is much less than the $N^2*N^2$ computations involved in the exhaustive method described earlier because the number of events, n, is much less than $N^2$, the number of pixels. One can determine higher order correlations, for example, third order, fourth order, etc. in a similar fashion. For an $m^{th}$ order correlation, all possible combinations of m events out of n(T) events may be considered, and a correlation function for these combinations given as: (# of times those m events occur together in a die)/(product of number of times each of them occur across all die)$^{1/m}$ may be determined.

In one example, let $\#p_1=100$, $\#p_2=75$, $\#p_3=50$, $\#(p_1, p_2)=60$, $\#(p_1, p_3)=40$, $\#(p_2, p_3)=35$, and $\#(p_1, p_2, p_3)=25$. In this example, $\#(p_i, p_j)$ indicates that events $p_1$ and $p_2$ tend to occur together more often than the combination of events $p_1$ and $p_3$ and the combination of events $p_2$ and $p_3$. In addition, events $p_1$ and $p_3$ tend to occur together more often than events $p_2$ and $p_3$. However, $\#(p_i, p_j, p_k)$ indicates that the three events tend to occur together less often than any combination of two of the events. The second and third order correlations for this example are $Corr[p_1, p_2]=60/\sqrt{7500}=0.69$, $Corr[p_1, p_3]=0.566$, $Corr[p_2, p_3]=0.57$, and $Corr[p_1, p_2, p_3]=25/(100*75*50)^{1/3}=25/72=0.347$. The correlation of a given set of defect events $\{p_1, p_2, p_3, \ldots\}$ is a function of threshold value, T. Ultimately, the correlation of any such set of points will approach unity (i.e., when all pixels are flagged as defects).

If one is interested in high order (say order 50) correlations of events that have a relatively large correlation value, these events may be located by keeping a list of lower order correlations that have a relatively large value of correlation, then these events may be "merged" to construct higher order correlations. For example, if all pair-wise correlations (e.g., order 2) are evaluated and $Corr[p_1, p_3]$ and $Corr[p_{12}, p_{27}]$ are determined to have relatively high values, the fourth order correlations $(p_1, p_3, p_{12}, p_{27})$ may be determined by examining the list of die in which $(p_1, p_3)$ and $(p_{12}, p_{27})$ occurred together. By determining higher order correlations for only those lower order correlations that had a relatively high value, relatively large correlations in higher order event groups may be identified without having to exhaustively search all combinations of events.

In one example, such a method may include sorting the list of first order event frequencies. The method may also include determining the second order co-occurrences of the n1 highest first order event frequencies. In addition, the method may include determining third and fourth order correlations for all (or at least some) pairs of the highest n2 second order events. The method may further include determining fifth, sixth, seventh, eighth, etc. order correlations by examining all (or at least some) pairs of the highest n3 third and fourth order events.

The above approach does not use design context associated with the die layout to discover systematic defect mechanisms. However, if the die layout is available, die regions can be classified into different design contexts (regions that have similar geometry layout and are, therefore, likely to be affected similarly by process variations). In this manner, the correlation accuracy can be improved, and the amount of computation can be significantly reduced by using the design context.

The methods described herein can, therefore, use design context to improve systematic defect detection. For example, in one embodiment, the method includes identifying different portions of die on the specimen having different design context. Therefore, the method may include segmenting the die regions based on design context. In addition, if a design context map is available, the peak events may be sorted by context. Such a method embodiment also includes determining if the properties of the individual pixels within the different portions having the same design context are correlated. In one such embodiment, the above second and higher-order correlation analysis may be performed only for events within a selected context. That is, no correlation computations may be performed between events that occurred in different contexts. This method reduces the number of event combinations to be analyzed and also improves the likelihood that if a relatively strong $n^{th}$ order correlation exists between peak events in the same context, a systematic defect generation phenomenon has occurred.

The method embodiments described herein may also be used to separate potential systematic defects from systematic nuisance defects (e.g., defects occurring at "cold spots" or non-critical areas (e.g., dummy structures, dummy fill areas, etc.) of the design that can result in systematic defects with little or no yield impact). The systematic nuisance defects may not be included in the output generated by the embodiments described herein. In other words, the systematic nuisance defects may not be presented to a user of the embodiments.

In one such embodiment, the method includes generating output illustrating the different portions having properties that are correlated. The output may include a display of one or more of the characteristics described herein (e.g., maximum difference, maximum intensity, etc.) at a specimen or stacked die level to the user. The output may also or alternatively include a display of highly correlated die frames belonging to the same design context type presented to the user.

The methods described above use correlations between peak events (potential defects) to identify systematic defect mechanisms. Thus, these methods include determining the exact location of the defects (e.g., by thresholding the difference histogram in some manner). One may perform this thresholding at various values of the threshold, T, in order to identify systematic defects that are "buried" in (or otherwise obscured by) the property of the individual pixels. Thresholding for locating peak events implies that one constructs difference histograms of all pixels in an image frame (say 512× 512). One alternative to this method is to use the histograms themselves to identify these correlations without having to explicitly find defect locations. Of course, this method does not possess the location accuracy obtained by matching exact defect locations. However, this method has the advantage that correlating frames rather than individual events may be computationally more efficient, especially if one wants to find highly correlated events at a continuum of threshold values, $T_1, T_2, \ldots T_n$.

In a further embodiment, monitoring the characteristic of the specimen includes determining if the characteristics of the individual regions within two or more die on the specimen are correlated. In this manner, the method may include determining if property measures within a die are highly correlated. Determining if the characteristics of the individual regions within two or more die on the specimen are correlated may be performed as described herein. In some embodiments, monitoring the characteristic of the specimen includes identifying portions of two or more die on the specimen in which the characteristics of the individual regions are correlated as locations of a potential systematic defect causing mechanism on the specimen. Identifying portions of two or more die on the specimen in which the characteristics of the individual regions are correlated may be performed as described herein. Such a method may also include displaying highly correlated die regions (e.g., frames) to the user as being possible sites at which some systematic defect causing mechanism may be at work.

If context maps or other context information of the die layout are also available, the method may use frame correlation and design context to determine the correlations. In particular, if pixels in a frame are sorted by design context and difference histograms for each context are recorded, then one can correlate frame histograms rather than individual defect events and obtain a reasonably accurate detection of systematic events that affect pixels belonging to a given context. For example, in another embodiment, monitoring the characteristic of the specimen includes identifying different portions of die on the specimen having different design context. Therefore, the method may include segmenting the die regions based on design context. Such a method embodiment also includes determining if the characteristics of the individual regions within the different portions having the same design context are correlated.

Sorting the characteristics in this approach by context may be more useful than determining if there is a correlation between characteristics of individual regions without using the design context. For example, a frame may contain defects in vastly different contexts and correlating frame characteristics that include multiple contexts may lead to misleading conclusions. In particular, different contexts may exhibit different characteristics, and determining the correlations across multiple contexts may make identifying particular characteristics associated with particular systematic defect mechanisms more difficult.

In one example of the above embodiment, for a given context, k, a given die, i, and a given frame, j, within the $i^{th}$ die, we can assume that we have recorded a difference histogram, $H_k(i, j, g)$ of gray levels, obtained either from a die-to-die or die-to-golden die comparison after image frame alignment. The index, g, gives the absolute value of the gray level difference (e.g., g has a range between from 0 to 255). Thus, $H_k(i, j, g)$ is the number of pixels in context k, in the $j^{th}$ frame of die i that have a gray level difference of g. Let $P_k(i, j, g, \Delta)$ be the number of pixels in the histogram in the gray level interval [g, g$\Delta$]. This value is the number of pixels that have a gray level difference of between g and g$\Delta$, where $\Delta$ is some relatively small interval of gray levels. The interval is used because certain events may show up only when the threshold is lowered below some value and we want to identify defect events by the gray level difference at which they are just detected.

Given the above definitions, let us imagine a specimen map in which each die is composed of frames and one can visually "light up" (or otherwise indicate) frames within each die that satisfy a certain correlation threshold. For example, suppose for a given context, k, and interval [g, gΔ], one were to light up all frames in which the value of $P_k(i, j, g, \Delta)$ is non-zero but less than (for example) 5 pixels. The selected frames are rough locations within a die belonging to the same context at which the difference signal falls within this gray level interval. If correlations between such frames across all die (analogous to the method described above for peak events) are now determined, then a high order correlation suggests that the same set of frames has events that fall in this gray level interval. The co-occurrence of events belonging to the same context, therefore, suggests a systematic mechanism at work. Such high order correlations could be highlighted (or otherwise indicated) in the display. As the gray level interval is varied over its range, potential systematic signatures may be detected for a given context, k. The method may be performed for each context to identify systematic signatures in each context.

The reason for choosing frames where the pixel count within the Δ interval is relatively small is because if there are a relatively large number of events, it is possible that we are looking at some process variation such as local color variation that affects many pixels within a frame rather than some defect mechanism that affects only a few pixels. Of course, there is no guarantee that the above statement is true. For example, local CD variations in a region can cause the pixel count in a given gray level interval to be relatively large, and this variation may be a defect that the user wishes to detect.

This method has some advantages in terms of memory and computation requirements. For example, the storage and computation costs of the event-based versus frame-based approaches to correlation analysis may be compared. For 100 die on a specimen, each 40 mm×40 mm assuming a 512×512 frame, there are about 95 million frames in total, about 1 million frames per die assuming an 80 nm pixel size. Assuming even 3 pixels per frame, if 1% of the frames contained defects, storing the (x, y) locations of all defects would require (0.01*100,000,000*3*8)=24 Mbytes per context for a given gray level interval. Since a frame index can be stored in 4 bytes and since individual pixels are not recorded, the storage required is 4 Mbytes per context for a given gray level interval. Moreover, this number is independent of the number of flagged pixels per frame. Computation-wise, the ratio of number of flagged defects to be correlated versus flagged frames to be correlated will determine the efficiency gained using the frame-based approach.

In one such embodiment, the method includes generating output illustrating the different portions having characteristics of the individual regions that are correlated. The output may also or alternatively include a display of one or more of the characteristics described herein (e.g., maximum difference, maximum intensity, etc.) at a specimen or stacked die level presented to the user. The output may also or alternatively include a display of highly correlated die frames belonging to the same design context type presented to the user.

The embodiments described herein have a number of advantages over currently used methods and systems for monitoring a characteristic of a specimen. For example, haze maps can be generated on currently used unpatterned wafer inspection systems. Such haze maps have been previously used to monitor surface roughness and unpatterned wafers. Such methods do not address patterned wafers or some of the pattern-specific information that can be determined by the embodiments described herein. In addition, some currently used inspection systems are specifically targeted at macro-defects. Some events that can be detected by such inspection systems can be detected using the embodiments described herein, but others that can be detected by the embodiments described herein cannot be detected on the macro-defect inspection systems since such systems do not have the resolution of the smaller-pixel inspection tools. Furthermore, the use cases described herein do not lend themselves to macro-defect inspection tools since specific device regions can be targeted by the higher resolution tools. Some currently used inspection systems can generate wafer and die macro views. However, such macro views are only used in setup to choose parameters of the inspection system like polarization. The macro views are not presented as part of the inspection results and are not used in any other manner.

In contrast, the embodiments described herein can be used to measure pattern property variations on a specimen, which directly correlate to systematic defects such as, for example, CD variation. In such an example, the specimen may be inspected by an inspection system and defects may be detected as before, but at the same time a CD variation signature map may be generated. Depending on how the map changes in amplitude or signature shape, an additional SPC flag may alert the user to check for CD variation using a metrology tool such as a CD scanning electron microscope (CD SEM). The location information from the inspection system may be used to move the metrology tool field of view above the specific parts of the die with the biggest CD variations (likely not where the user would look with their CD SEM as a matter of course).

Such an application of the embodiments described herein may increase in importance as reticle enhancement techniques (RET) cause looking at only one spot per die in metrology to no longer be an acceptable proxy for monitoring the process window. Moreover, the recent RET issues and shrinking design rules mean that more systematic defects may be present on a specimen, which are often manifested as a change in some property measured by the inspection systems. As described further herein, the embodiments described herein advantageously utilize output generated by inspection systems to detect and monitor systematic defects on the specimen.

The embodiments described herein are also advantageous in that they provide more value to the user with minimal to zero throughput impact to the inspection process. For example, the embodiments described herein can be used to identify problems that could not be detected using currently used systems and methods. In this manner, the embodiments described herein can be used to provide better (e.g., more accurate, more sensitive, etc.) process monitoring and control. In addition, the embodiments described herein can be implemented using any currently available inspection system. In particular, the embodiments can be implemented using any optical or electron beam hardware of any currently used inspection system.

Another embodiment relates to a computer-implemented method for generating an image of a surface of a patterned wafer. In some embodiments, the computer-implemented method may be implemented by program instructions executable on a processor. The program instructions and the processor may be further configured as described herein. For instance, the program instructions may be included in a carrier medium, which may be configured as described herein. In addition, the computer-implemented method may be performed by any of the systems described herein.

The method includes acquiring output of an inspection system for the patterned wafer. The inspection system may be configured as described further herein. The output may include any output of the inspection system. In one embodiment, acquiring the output includes acquiring the output of the inspection system for the patterned wafer using optical pattern suppression. In one such embodiment, the optical pattern suppression includes Fourier filtering. In this manner, the acquiring step may include using a Fourier filter during image acquisition. The Fourier filter may include any suitable Fourier filter known in the art. In addition, Fourier filtering may be performed in any suitable manner known in the art. In some embodiments, during recipe setup, Fourier filter training may be performed prior to setting up the defect detection algorithm thresholds. Fourier filtering training may be performed in any suitable manner. In addition, setting up the defect detection algorithm thresholds may be performed in any suitable manner.

Once Fourier filter training has been performed, one of the use cases described herein may be performed. For example, in one embodiment, the acquiring step includes acquiring the output for substantially an entire surface of the patterned wafer. The output may be acquired for substantially an entire surface of the patterned wafer in any suitable manner (e.g., by scanning substantially the entire surface of the wafer). In one such embodiment, to generate a surface image as described further herein, a user may invoke a full wafer image scan. The full wafer image scan may then be executed by the inspection system using the existing optics set in the recipe.

The method also includes generating the image of the surface of the patterned wafer using the output. The image may be generated using the output in any suitable manner. In addition, the image may have any suitable image format. In one embodiment, the image of the surface of the patterned wafer includes an image of substantially an entire surface of the patterned wafer. For example, as described above, the output may be acquired for substantially an entire surface of the patterned wafer. In this manner, such output may be used to generate an image of substantially the entire surface of the patterned wafer. As such, the method may include generating a patterned, full wafer surface image, which may be used as described further herein. In particular, the embodiments described herein may use optical pattern suppression to assemble a useable full wafer image of a patterned wafer.

In another embodiment, the image of the surface of the patterned wafer is substantially free of pattern misregistration noise. For instance, by using the Fourier filter during output acquisition, a full wafer image may be obtained that is substantially free of pattern misregistration noise which typically dominates existing surface images. In particular, the embodiments described herein eliminate pattern misregistration noise that may be present in images of patterned wafers that are generated by subtracting images acquired at different positions on the wafer to thereby cancel contributions from patterned features on the wafer in the images. However, in order to perform such image subtraction, the images have to be aligned to each other prior to image subtraction. Therefore, the images generated by such image subtraction may include noise from patterns that are not perfectly registered to each other. In contrast, since the image of the patterned wafer described herein is not generated by subtracting one image from another, the image of the patterned wafer will contain substantially no pattern misregistration noise. In particular, the embodiments described herein eliminate residual pattern noise from patterned wafer surface images by using optical Fourier filtering to eliminate the pattern from the image prior to digitization. Therefore, the embodiments described herein can be used to obtain a superior patterned wafer surface image without pattern noise dominating the image. As such, the embodiments described herein may generate patterned wafer imagery that can serve as a "proxy" for the wafer underlying the patterned features.

In an additional embodiment, the image of the surface of the patterned wafer includes a gray scale image of intensity of light scattered from the patterned wafer. For example, the image may include a gray scale image of the intensity response off of the wafer. In addition, if the output is acquired using optical pattern suppression, the image may include a gray scale image of intensity of light scattered from the surface of the wafer. In a further embodiment, the image of the surface of the patterned wafer includes a noise map of the surface of the patterned wafer. The noise may include any of the noise described herein. In addition, the noise map may be configured as described herein.

In some embodiments, generating the image includes determining one or more statistics for one or more regions of the patterned wafer in which the output is acquired using optical pattern suppression. In one such embodiment, the image includes a gray scale image of the one or more statistics. For example, each frame (job) of the scan of the wafer performed by the inspection system may record a statistic from the region being Fourier filtered. The region(s) of the wafer may be further configured as described herein. The statistic can include any suitable statistic including any of those described further herein, but may usually be the peak intensity or a cumulative density point in a histogram for a region. The statistics may be determined in any suitable manner. The statistics from each frame can be collected and displayed in a gray scale image format.

In some embodiments, generating the image includes dividing one or more regions of the patterned wafer in which the output is acquired using optical pattern suppression into one or more sub-regions and determining one or more statistics for the one or more sub-regions. The statistic(s) for the sub-region(s) may include any of the statistics described herein and may be determined in any suitable manner. In one such embodiment, the image includes a gray scale image of the one or more statistics. Therefore, a region as described above may be divided into sub-regions, and a statistic may be recorded for each sub-region thereby providing more image detail. The regions may be divided into sub-regions in any suitable manner. As described above, the statistics from each frame may be collected and displayed in a gray scale image format.

In one embodiment, the generating step includes determining if one or more regions of the patterned wafer are not suitable for optical pattern suppression and removing images corresponding to the one or more regions from the image of the surface. For example, because the full wafer image may be already highly decimated for visualization, areas of the wafer that are not suitable for Fourier filter pattern suppression can be discarded. The areas of the wafer that are not suitable for Fourier filter pattern suppression may include areas of the wafer in which periodic patterned features are not formed or in which patterned features that produce patterns that cannot be substantially completely removed from the output by optical pattern suppression are formed. The areas of the wafer that are not suitable for Fourier filter pattern suppression may be determined in any suitable manner (e.g., by applying a threshold to different regions in the image).

In another embodiment, the generating step includes determining one or more statistics in only regions of the wafer or dies on the wafer in which the pattern is optically suppressed. The statistics for the regions may be determined as described above and may include any suitable statistics known in the art. In this manner, the acquiring step of the method may include suppressing the pattern formed on the wafer from the noise map for a patterned wafer generated by the method by applying an optical Fourier filter during image acquisition, and generating the image may include recording only those statistics in the optically Fourier filtered regions of the die(s) or the wafer.

In one embodiment, generating the image includes generating noise maps of dies formed on the patterned wafer. For example, generating the noise maps of dies formed on the patterned wafer may include generating a noise map of the surface of the patterned wafer and then separating the noise map of the "full" patterned wafer into different noise maps corresponding to different dies formed on the wafer. The "full" patterned wafer noise map may not necessarily correspond to the entire patterned wafer. For example, the "full" patterned wafer noise map may not include portions of the patterned wafer adjacent to the edge of the patterned wafer. The full patterned wafer noise map may be divided into individual die noise maps using any suitable information (e.g., information about a layout of dies formed on the wafer, output acquired by the inspection system if the output for spaces and/or boundaries between dies can be differentiated from each other, etc.). In addition, the patterned wafer noise map may be separated into die noise maps after the output for the wafer has been acquired. Alternatively, the patterned wafer noise map may be separated into die noise maps as the output for the wafer is being acquired (e.g., in real time) based on the information described above possibly in combination with information about how the output is acquired (e.g., swath information). The noise maps for the dies may also be generated according to any other embodiments described herein.

In one such embodiment, the method includes comparing the noise maps to one or more other noise maps of dies to accept or reject individual dies on the patterned wafer. In this manner, the method may include comparing die noise maps to other die noise maps to accept or reject individual die. The other die noise maps that are compared to the die noise maps may include any of the die noise maps described herein. The noise maps of different dies may be compared as described above to determine if the pattern has been equally or sufficiently suppressed in noise maps for the different dies such that die noise maps in which the pattern has not been suppressed equally or sufficiently can be rejected. In addition, or alternatively, the die noise maps for different dies may be compared to identify dies that are defective in some manner (e.g., dies that exhibit a die-level defect or process signature). In this manner, the noise maps may be compared to identify dies that are outliers, are defective, or are unique in some manner compared to other dies on the wafer or on other wafers. The die noise maps for different dies may be compared as described further herein. Furthermore, wafer noise maps may be compared in a similar manner and for similar reasons (e.g., to identify wafer noise maps in which the pattern has not been sufficiently suppressed, to identify outlier wafer noise maps, to identify wafer noise maps that contain a wafer-level defect or process signature, etc.).

In another embodiment, the method includes comparing the noise maps of dies formed on the patterned wafer to one or more other noise maps of dies. In one such embodiment, the one or more other noise maps include the noise maps of the dies on the patterned wafer. In this manner, the method may include comparing die noise maps to other die noise maps on the same wafer. In another such embodiment, the one or more other noise maps include noise maps of dies on other patterned wafers. In this manner, the method may include comparing die noise maps to other die noise maps on other wafers. The die noise maps on different wafers may be compared as described further herein. For instance, once the die noise maps have been generated, alignment of different die noise maps to one another, whether those die noise maps were generated for dies on the same patterned wafer or different patterned wafers, can be performed relatively easily. After the different die noise maps have been aligned to one another, the die noise maps may be compared. In an additional such embodiment, the one or more other noise maps include a composite of multiple die noise maps from a full patterned wafer noise map. As such, the method may include generating the one or more other die noise maps through a composite of multiple die noise maps from a full wafer noise map. For example, the composite of the multiple die noise maps may be generated using an averaging technique to essentially combine the die noise maps across an entire wafer. In a similar manner, a composite may be generated using multiple die noise maps from noise maps for more than one wafer. Generating a composite of multiple die noise maps may, therefore, essentially average out any abnormal noise in the individual die noise maps thereby making the composite noise map a better representative of a normal die noise map. In this manner, the composite die noise map may be a better "reference" die noise map for comparison to the die noise maps for the patterned wafer under test. In a similar manner, a composite wafer-level noise map may be generated (e.g., using multiple wafer-level noise maps for different wafers) and used as described herein.

In some embodiments, generating the image includes generating noise maps of dies formed on the patterned wafer, and the method includes generating a composite noise map from all of the noise maps of the dies on the patterned wafer and comparing the composite noise map to one or more other noise maps of dies. In this manner, the method may include generating a die noise map through a composite of multiple die noise maps from a "full" wafer noise map. Therefore, the generating step may include generating a composite die noise map for the wafer under test. The one or more other noise maps of dies compared to the composite noise map may also be a composite of two or more die noise maps. In this manner, the comparison step described above may be a composite to composite comparison. Alternatively, the one or more other noise maps may be a noise map generated for a single die on a single wafer or may be any other reference described herein. Comparing the composite die noise map for the wafer under test to one or more other noise maps of dies may be performed for any of the reasons described herein (e.g., to detect a die-level defect and/or pattern signature) in the composite die noise map.

In one embodiment, the patterned wafer includes a test patterned wafer. In one such embodiment, generating the image includes generating noise maps of dies formed on the patterned wafer. The noise maps of the dies may be generated as described herein. In some such embodiments, the method includes generating a composite noise map of multiple die noise maps from a full patterned wafer noise map and storing the composite noise map as a golden die noise map for comparison to the noise maps of the dies formed on the test patterned wafer. In this manner, the method may include generating a die noise map through a composite of multiple die noise maps from a full wafer noise map. A golden die noise map may then be stored for comparison with the current wafer or any other wafers. For example, a composite noise map of multiple die noise maps may be generated for a patterned wafer, and then individual die noise maps generated for the wafer may be compared to the composite noise map. In this manner, as described further herein, the composite noise map may be a more suitable reference than any single die noise map, and such a composite noise map may be used as a self-reference for the wafer under test.

In some embodiments, the surface image generated as described above may be displayed to a user. The surface image may be displayed to the user in any suitable manner. The user may examine the surface image for the appearance of a defect or process signature. The user may then tune a detection algorithm to pull out the signature.

In some embodiments, generating the image includes generating noise maps of dies formed on the patterned wafer, and the method includes displaying the noise maps with design information overlaid thereon such that noise is displayed as a function of die functional region. For example, noise maps may be displayed overlaid with GDSII design information or any other design information described herein in order to view the noise as a function of die functional region. Since the design information is being overlaid with die noise maps, the design information and the die noise maps can be aligned to each other for overlay relatively easily. The design information that is overlaid with the die noise maps may be illustrated in any suitable manner (e.g., with indicators for just the different die functional regions, with indicators for any other information about the die design, etc., or some combination thereof). The noise maps with the design information overlaid thereon may be displayed in any suitable manner (e.g., using any suitable user interface and any suitable display device).

In an additional embodiment, the image of the surface of the patterned wafer includes a noise map of the surface of the patterned wafer, and the method includes displaying the noise map with one or more attributes determined by the inspection system overlaid thereon. For example, the method may include combining a wafer noise map display with other attribute(s) generated on the inspection system. The wafer noise map and the other attribute(s) may be overlaid on each other in the same user interface screen on any suitable display device. The one or more attributes that are overlaid with the noise map may include any attributes that are determined by the inspection system with some reference to the wafer position. In this manner, the noise map and the attribute(s) can be overlaid with each other easily based on the positions or coordinates corresponding to the noise map and the attribute(s). The one or more attributes determined by the inspection system may include one or more attributes of defects (e.g., light point defects) detected on the patterned wafer, one or more attributes of the wafer determined by the inspection system, one or more attributes of the inspection performed by the inspection system, etc. For example, the attribute(s) may include a defect map, care area region boundaries, die boundaries, swath boundaries, inspection region boundaries, image intensities, etc. Therefore, displaying the noise map with the attribute(s) overlaid thereon may provide significant information to a user such as the noise exhibited by different care areas, the noise exhibited by the same care areas at different positions on the wafer, any correlation between individual defects and noise, the noise exhibited by dies at different positions on the wafer, etc.

In a further embodiment, the image of the surface of the patterned wafer includes a noise map of the surface of the patterned wafer, and the method includes simultaneously displaying the noise map and one or more attributes determined by the inspection system. For example, the method may include combining a wafer noise map display with other attribute(s) generated on the inspection system. The wafer noise map and the other attribute(s) may be displayed simultaneously (e.g., side-by-side) in the same user interface screen. The user interface and a display device in which the user interface is displayed may have any suitable configuration. In this manner, the wafer noise map and the other attribute(s) may be displayed separately and simultaneously without overlaying the map and the attribute(s) as described above. The attribute(s) may include a defect map, care area region boundaries, die boundaries, swath boundaries, inspection region boundaries, image intensities, etc. Displaying the noise map and the one or more attributes in this manner may also provide significant information to the user including any of the information described above. In addition, one or more of the attributes described above may be overlaid with the noise map and one or more of the attributes described above may be displayed separately (e.g., next to) the overlaid noise map. In this manner, method may include displaying different attributes, at least one of which is overlaid with the noise map and at least one of which is not overlaid with the noise map, at the same time.

In some embodiments, the method includes determining if a defect signature is present in the image without applying a threshold for defect detection to the image. For instance, the images generated as described herein are detection algorithm independent. In other words, the images described herein are not generated by applying a defect detection algorithm to the acquired output of the inspection system. Therefore, the embodiments described herein may use the surface image for defect signature exploration without applying an algorithm to threshold defects into a binary image. The defect signature may include any suitable defect signature including any of the signatures described herein. Determining if a defect signature is present in the image may be performed without identifying the defect signature. In other words, determining the presence of a defect signature may simply include determining whether or not a defect signature is present in the image regardless of whether or not the defect corresponding to the defect signature is known. In a similar manner, in some embodiments, the method includes determining if a process signature is present in the image without applying a threshold for defect detection to the image. The process signature may be any suitable process signature including any of the signatures described further herein, which may vary depending on the process corresponding to the signature. The process may include any process that can be performed on the wafer.

In another embodiment, the method includes determining if a defect signature is present in the image without tuning a defect detection algorithm. For example, since as described above the surface image may be a gray scale image of the intensity response off of the wafer, the method may include exploring the image generated as described herein without tuning a defect detection algorithm. In addition, the embodiments described herein may use superior suppression of pattern noise resulting in a proxy for bare surface measurement. Therefore, no algorithm tuning is required to identify defect signatures. In contrast, often signatures are missed when the algorithm fails to pull out the defects that make up the signature. As such, the signature may go unnoticed. However, the embodiments described herein may perform defect signature exploration to catch signatures that could have otherwise gone unnoticed.

In some embodiments, the method includes applying SSA to the image to determine if a defect signature is present in the image. For example, an SSA algorithm may be applied to a surface image of the patterned wafer to flag signature alarms. SSA may be performed as described further herein.

In one embodiment, the method includes identifying a defect signature present in the image without applying a threshold for defect detection to the image. For instance, the images generated as described herein are defect detection algorithm independent. In other words, the images described herein are not generated by applying a defect detection algorithm to the acquired output of the inspection system. Therefore, the embodiments described herein may use the surface image for defect signature identification without applying an algorithm to threshold defects into a binary image. In addition, the embodiments described herein can be used to perform defect signature identification to catch signatures that could have otherwise gone unnoticed. In an additional embodiment, the method includes identifying a process signature present in the image without applying a threshold for defect detection to the image. In this manner, the embodiments described herein may be used to identify process signatures and defectivity signatures on patterned wafers through the use of an optical pattern suppression filter (a Fourier filter). The process signature and the defectivity signature may include any of the signatures described herein.

In some embodiments, the method includes determining an optics mode of the inspection system to be used for the acquiring step such that the image can be used for detecting a selected defect signature. In another embodiment, the method includes determining, without tuning a defect detection algorithm, an optics mode of the inspection system to be used for the acquiring step such that the image can be used for detecting a selected defect signature. For example, the method may include using the image generated as described herein to determine the best optics mode for highlighting a wafer defect signature without concentrating on specific defects of interest. In this manner, the surface images described herein may be used to select the best optics mode for highlighting defect signatures of interest. In addition, the optics mode of the inspection system can be selected without tuning the defect detection algorithm since the images are generated without using a defect detection algorithm. Therefore, the mode selecting may be performed as described above without tuning a defect detection algorithm thereby reducing the time involved in setup. The optics mode may include any suitable optics mode of any suitable inspection system.

In one embodiment, the method includes performing the acquiring step using more than one optics mode of the inspection system, generating more than one image of the surface of the patterned wafer using the output acquired using the more than one optics mode, and using the more than one image to determine an optics mode of the inspection system to be used for the acquiring step such that the image can be used for detecting a selected defect signature. The more than one optics mode may include each available optics mode of the inspection system or only a subset of all of the available optics modes of the inspection (e.g., only those optics modes that are known to be suitable for the patterned wafer). In this manner, a surface image may be generated as described herein for each optics mode of the inspection system, and the surface images for each mode are acquired without the need for tuning a defect detection algorithm. In other words, since the images described herein are generated without applying a defect detection algorithm to the output acquired by the inspection system, there is no need for tuning a defect detection algorithm to generate the surface images and therefore no need for tuning a defect detection algorithm to determine the best optics mode for detection of a defect signature in the image.

The surface images can also be generated for each optics mode and shown to the user in an image gallery of a user interface. The surface images may be shown to the user in any suitable manner. Image metrics may be determined for the images (such as signature density or contrast) to identify the best mode to pull out or suppress a signature. Some of the use cases described herein assume some prior knowledge of the desirability of the signature. In some cases, the signature is desirable, and it is desirable to highlight the signature in the image. In other cases, the signature is a nuisance, and the goal is to suppress the signature in the image. Therefore, some prior expertise of the tool user is useful to interpret signatures that are detected as described herein.

In one embodiment, the image of the surface of the patterned wafer includes a noise map of the surface of the patterned wafer. The noise map of the surface of the patterned wafer may include any of the noise maps described herein and may be generated as described further herein. In one such embodiment, the method includes performing the acquiring step using more than one optical configuration of the inspection system. The more than one optical configuration may include at least two optical configurations that are different in at least one optical parameter of the inspection system. The at least one optical parameter of the inspection system may include any variable or adjustable optical parameter of the inspection system (e.g., wavelength, polarization, aperture configuration, etc.). Such a method may also include generating more than one noise map of the surface of the patterned wafer using the output acquired using the more than one optical configuration. In this manner, the method may include generating more than one noise map, each of which is generated using the output acquired using one of the optical configurations. In addition, such a method may include using the more than one to noise map to identify wafer-scale process variation as a function of the more than one optical configuration. Such a method may further include using the wafer-scale process variation as a function of the more than one optical configuration to identify a best optics mode for the combination of the inspection system and the patterned wafer. In this manner, the embodiments described herein may include using the noise map to describe wafer-scale process variation as a function of the inspection system optical configuration. This information can be used to select or develop the best optical mode of the inspection system for a given process and/or for a given wafer-scale process variation. For example, the optical mode and/or configuration that provides the best or most accurate detection of the wafer-scale process variation may be selected or created as the best optics mode.

In another embodiment, the image of the surface of the patterned wafer includes a noise map of substantially an entire surface of a test patterned wafer on which a process was performed. The process may include any process that may be performed on a patterned wafer such as lithography, etch, chemical-mechanical polishing (CMP), deposition, cleaning, etc. The noise map may include any of the noise maps described herein and may be generated as described further herein. In some such embodiments, the method includes performing the acquiring step for multiple patterned wafers on which the process was performed using one or more different parameters of the process. The different parameters of the process may include any parameters of the process that may be varied. For example, different patterned wafers may be processed using different focus conditions of a lithography process, different exposure conditions of the lithography process, different etch times, different CMP rates and/or times, or any combination thereof. Such a method may also include generating noise maps of the surfaces of the multiple patterned wafers using the output. The noise maps may be the same type of noise maps as that of the patterned wafer under test. The noise maps for the multiple patterned wafers may also be generated in the same manner as the noise map for the patterned wafer under test. In addition, such a method may include storing the noise maps of the surfaces of the multiple patterned wafers as a function of the one or more different parameters. In this manner, the method may include saving full wafer noise maps from each inspection point under one or more control conditions. For example, the noise maps for different patterned wafers may be stored such that they are associated with the different parameters used to process the different patterned wafers. As such, the different noise maps may be correlated to the different parameters thereby essentially calibrating the different noise maps to the different parameters. Such a method may further include comparing the noise map for substantially the entire surface of the test patterned wafer with the stored noise maps to determine one or more characteristics of the process performed on the test patterned wafer. For example, the stored noise maps may be compared with a noise map for the current wafer to determine a characteristics of the process. Characteristics of the process that may be determined include, but are not limited to, matching of two or more process tools (e.g., whether or not two or more process tools are performing the same process differently), flagging (or identifying) process excursions, and process metrics (e.g., line width changes, etch uniformity, CMP signature, etc.) by correlating the noise map features to maps generated under known conditions.

In another embodiment, the method includes tuning one or more optical parameters of an inspection recipe used for the acquiring step by performing the acquiring step and the generating step using each possible optical configuration of the inspection system and using the images corresponding to each possible optical configuration to select an optical configuration for the inspection recipe based on a presence or non-presence of defect signatures in each of the images. In this manner, the method may include tuning inspection recipe optical parameters by acquiring a noise/defectivity map under each possible optical configuration and using these noise/defectivity maps to select a desired optical configuration based on the presence or non-presence of defect signatures in each noise/defectivity map. The optical parameters may include any optical parameters of the inspection system (e.g., any adjustable optical parameters of the inspection system). In this manner, the parameters of the inspection system and inspection recipe that may be selected or tuned in the embodiments described herein may include optics mode and/or any other optical parameters of the inspection system that can be used to acquire the output.

In an additional embodiment, the acquiring step is performed using a predetermined optical configuration of the inspection system. In one such embodiment, the method includes tuning one or more parameters of a defect detection algorithm of an inspection recipe by matching a presence or non-presence of defect signatures in the image to output of the defect detection algorithm. In this manner, the method may include tuning inspection recipe detection algorithm parameters by using a noise/defectivity map to show the presence or non-presence of defect signatures under a given optical configuration to match the output of the defect detection algorithm. Therefore, the embodiments described herein may include selecting one or more parameters of defect detection performed using one or more of the images described herein. In addition, the embodiments described herein may include selecting one or more parameters of image acquisition (e.g., the one or more optical parameters) and one or more parameters of defect detection. Selecting the one or more optical parameters and/or one or more parameters of defect detection as described above may advantageously increase the accuracy with which the defect and/or process signatures may be detected and identified in the images generated as described herein.

The embodiments described herein have a number of advantages over other methods and systems for generating surface images of wafers and using such images. For example, existing surface image methods for patterned wafers utilize a display of raw image intensities or die-to-die difference image intensities to obtain a wafer image. In addition, existing defect signature detection requires proper optics mode selection and proper setting of detection algorithm parameters. Furthermore, existing mode selection uses known defect signal-to-noise (S/N) measurements. The optics mode that maximizes defect S/N and minimizes noise is typically selected.

However, such methods and systems have a number of disadvantages. For example, in patterned wafer imagery, a primary source of nuisance noise is the pattern geometry itself. In addition, die-to-die image subtraction is the most common way to suppress the pattern and display the residual process or defectivity information. However, residual misregistration noise is difficult to separate from process noise and CD variation. Furthermore, signature detection currently depends on examining a defect map for a spatial signature in the pattern of defects. If the algorithm is not properly tuned, the signature can be missed. Algorithm tuning has been shown to be crucial to pulling out signatures.

In contrast to the methods and systems described above, the embodiments described herein can advantageously eliminate residual pattern noise from confusing the interpretation of patterned wafer surface images by using optical Fourier filtering to eliminate the pattern from the image prior to digitization. In addition, the embodiments described herein can be implemented on commercially available inspection systems with appropriate modifications. For example, the Puma 90xx and 91xx series of tools are well-suited for the applications described herein since the inspection results of such systems rely heavily on suppression of patterns for defect detection.

Embodiments described further herein generally relate to methods and systems for wafer signature inference. As described above, the image of the surface of the patterned wafer may include a noise map of the surface of the patterned wafer. The noise maps may be generated according to any of the embodiments described herein using output acquired by any of the inspection systems described herein (e.g., BF systems and/or DF systems). In one such embodiment, the method includes identifying a signature, which corresponds to only the last process performed on the patterned wafer before the output is acquired, in the noise map. In other words, the signature that is identified is the signature for the current process (e.g., the process being monitored using the generated image) or the signature for the current layer of the patterned wafer. The signature that corresponds to only the last process performed on the patterned wafer may be identified as described further herein.

In this manner, the methods described herein may include de-convolving wafer noise images and/or maps generated using wafer inspection systems into practical and relevant manufacturing process control signals. For example, as with defect detection, the generation of wafer scale images involves the acquisition of optical signals that may be a function of all of the processing that has occurred on the wafer to date. As such, the image and thus signatures extracted from the image may include artifacts from numerous sources of variation, some of which may not be of interest for a given application.

The utility of the signature is, therefore, going to vary depending on whether the signal from specific source(s) of process variation can be isolated. Since a signature in the noise map for a current layer of the wafer can be isolated from other signatures as described herein, which may be attributable to processes other than the one being monitored using the acquired output, that may be present in or affect the noise map, the signatures identified as described herein have practical uses for process control and other applications described herein. In this manner, the signatures identified in the embodiments described herein can be used as practical manufacturing control signals.

In some embodiments, the method includes identifying a signature, which corresponds to only the last process performed on the patterned wafer before the output is acquired, in the noise map based on one or more other signatures corresponding to one or more other processes performed on the patterned wafer. In this manner, the signature corresponding to only the last or most recent process performed on the patterned wafer can be identified by considering the signatures from previous process levels that are not relevant to the current process step (e.g., the process step that is being monitored). For example, information about the signatures corresponding to previous processes and/or the previous process signatures themselves may be used to determine if any signature for the current process is present in the noise map and/or wafer image. In addition, information about the signatures corresponding to previous processes and/or the previous process signatures themselves may be used to separate previous process signatures from any current process signatures present in the noise map and/or wafer image.

In another embodiment, the method includes identifying a signature, which corresponds to only the last process performed on the patterned wafer before the output is acquired, in the noise map by extracting one or more signatures corresponding to one or more other processes performed on the patterned wafer from the noise map. In this manner, the method may include subtraction or extraction of prior level signatures from the noise map. For example, all of the signatures in the noise map or wafer image may be additive (or may appear in the noise map or wafer image as a summation of all of the signatures). In other words, all of the signatures from the current level and previous levels may be superimposed on each other in the noise map and/or wafer image for the current level. In this manner, the previous process signatures may be simply subtracted from the noise map for the current process. However, if all or some of the signatures in the noise map or wafer image affect the noise map or wafer image for the current process in a more complex manner, then the previous process signatures may be extracted rather than simply subtracted from the noise map. Such extraction may include, for example, modifying previous layer signatures to account for the effects of the current layer on the previous layer signatures and then removing the modified previous layer signatures from the current layer noise map and/or any other suitable functions.

The method may also include searching for previous layer signatures in the noise map and/or wafer image such that if the previous layer signatures are not present in the noise map and/or wafer image, the previous layer signatures are not mistakenly subtracted or extracted from the noise map and/or wafer image thereby preventing unnecessary and/or undesirable modification of the noise map and/or wafer image. Searching for previous layer signatures in the noise map and/or wafer image may be performed by searching for the entire previous layer signature, searching for a portion of the previous layer signature that is unique to the previous layer signature, and/or determining if the noise map and/or wafer image has any one or more characteristics that are indicative of the presence of the previous layer signature.

After the previous layer signatures have been extracted from the noise map and/or wafer image, the signature for the current process may be extracted from the noise map and/or wafer image. The current process signature may be extracted from the noise map and/or wafer image as described further herein.

In an additional embodiment, the method includes identifying a signature, which corresponds to only the last process performed on the patterned wafer before the output is acquired, in the noise map and classifying the signature. In this manner, the method may include signature classification. Classifying the signature may be performed in any suitable manner (e.g., by extracting one or more features of the signature and classifying the signature based on the one or more features, by matching the signature to one or more previously classified signatures, by spatial signature analysis, etc.). Classifying the signature may be performed automatically by the embodiments described herein. The classification assigned to the signature may be used in any number of applications such as process monitoring, process control, root cause analysis, etc.

In a further embodiment, the method includes identifying a signature, which corresponds to only the last process performed on the patterned wafer before the output is acquired, in the noise map and comparing the signature to additional signatures to determine one or more characteristics of the patterned wafer or the last process. The additional signatures may be stored in a storage medium, which may include any of the storage media described herein. The additional signatures may be stored in a library or any other suitable data structure. In addition, the additional signatures stored in the library may be associated with different characteristics of the patterned wafer and/or different characteristics of the process. For example, one of the stored signatures may be associated with a patterned wafer that is warped, another of the stored signatures may be associated with a lithography process that is out of focus to some degree, another of the stored signatures may be associated with the lithography process that is out of focus to a different degree, etc. In this manner, the signature identified for the current process may be compared to other signatures to determine some information about the wafer and/or the process that may be used to monitor the process, control the process, correct the process, reject the wafer, re-work the wafer, etc.

The additional signatures may be associated with different characteristics of the patterned wafer and/or the process in a number of different manners. In one such embodiment, the additional signatures are generated empirically. In this manner, the additional signatures may be stored as one or more empirical signature source libraries. Empirically generating the additional signatures may be performed by processing wafers using different processes with different parameters of the processes and acquiring signatures for each of the wafers after each of the different processes. In addition, empirically generating the additional signatures may be performed by processing the wafers as described above and determining if the signatures are attributable to the process and its parameters and/or one or more characteristics of the wafer (e.g., warp) by performing one or more other measurements and/or processes on the wafer (e.g., stress measurements, CD measurements, defect review, etc.). Furthermore, empirically generating the additional signatures may be performed based on empirical knowledge of different processes and/or wafers, which may be acquired in any other manner.

In another such embodiment, the additional signatures are generated by modeling of one or more process tools used to perform the last process. In this manner, the additional signatures may be generated using process equipment models with predicted signatures. Modeling the one or more process tools may be performed in any suitable manner using any suitable models. The modeling may be performed to simulate one or more characteristics of the patterned wafer after processing by the one or more process tools. Generating the signatures in this manner may also include modeling how the inspection system will "see" the wafer. For example, based on the one or more simulated characteristics of the wafer that would be produced by the one or more process tools, modeling of the inspection system may be performed to simulate the output that would be acquired for the wafer. The additional signatures may then be extracted and/or otherwise identified in the simulated output.

In one embodiment, the method includes identifying a signature, which corresponds to only the last process performed on the patterned wafer before the output is acquired, in the noise map and determining if one or more parameters of the last process are out of process control limits based on the signature. In this manner, the method may include fault diagnostic methods that include signature recognition. For example, any of the signatures identified as described herein may be used to determine if the current process is out of process control limits. Determining if the current process is out of process control limits using the signature may include determining if the signature corresponds to a known signature or corresponds to an abnormal signature (e.g., a not previously observed signature or a signature that has one or more characteristics that are abnormal from those previously observed after the same process), comparing the signature to additional signatures such as those described above, some of which correspond to the process operating within control limits, others of which correspond to the process operating outside of the control limits, classification of the signature, or in any other suitable manner.

In another embodiment, the method includes identifying a signature, which corresponds to only the last process performed on the patterned wafer before the output is acquired, in the noise map and controlling one or more parameters of the last process based on the signature. In this manner, the method may include control methods that include signature recognition. Controlling the one or more parameters of the last process may be performed in a feedback manner such that additional wafers produced by the process have one or more characteristics that are more acceptable (or are closer to target values for the characteristic(s)). In addition, controlling the one or more parameters may be performed for processes that are out of control limits and/or processes that are operating within control limits (e.g., processes that are drifting from target performance but are not yet outside of control limits). Determining which parameter(s) should be controlled and how the parameter(s) should be controlled using the signature may be performed in any suitable manner. For example, the signature may be used to determine one or more parameters of the process corresponding to the signature, and then the determined one or more parameters may be compared to target or ideal parameters for the process to determine which parameter(s) should be altered and how those parameter(s) should be altered.

In some embodiments, the method includes identifying a signature, which corresponds to only the last process performed on the patterned wafer before the output is acquired, in the noise map based on raw data acquired for the patterned wafer prior to the last process and signatures identified in the raw data. The raw data and the signatures identified in the raw data may be stored in any suitable storage medium such as a database of historical raw data and extracted signatures. In this manner, the method may utilize historical data and extracted signatures to identify a signature for the last process performed on the wafer. In contrast, currently used methods for analyzing output are generally limited to data collected at the current state of the specimen. However, since processes performed on the wafer prior to the last process may affect the noise map, utilizing previously acquired output and/or signatures determined for the wafer to identify the signature for the current layer may increase the accuracy with which the signature corresponding to the last process can be identified in the noise map. For example, erroneous conclusions can be drawn if one assumes that the signature extracted from the current state of the specimen is attributable to the current/recent process steps.

The embodiments described herein may be used for applications similar to defect source analysis (DSA) type applications. For example, DSA type applications are used to identify where in a process flow defects have originated. Identifying where in the process defects have originated has two general purposes. For example, identifying where in the process defects have originated may be performed for root cause analysis in which an investigation is being performed to identify a problem step in the process. In addition, identifying where in the process defects have originated may be performed for process monitoring where interest is limited to those defects generated at the current process step.

In one embodiment, the method includes identifying a signature, which corresponds to only the last process performed on the patterned wafer before the output is acquired, in the noise map and determining a root cause corresponding to the signature. In this manner, the wafer image signatures may be used for root cause analysis to identify where in a process a given signature has originated. The root cause analysis may be performed as described further herein (e.g., comparing the signature for the current process to a library of signatures), and the results of the root cause analysis may be used for any application described herein (e.g., process control and correction).

In another embodiment, the method includes identifying a signature, which corresponds to only the last process performed on the patterned wafer before the output is acquired, in the noise map and monitoring the process based on the signature. In this manner, the wafer image signatures may be used for isolating signatures that were generated at the current level of the process. In addition, since the current process signature can be isolated from previous process signatures, process monitoring performed using the signatures identified as described herein may be substantially accurate. Any processes performed on the patterned wafer may be monitored using the signatures described herein. The signatures may be used for process monitoring as described farther herein (e.g., to monitor the process by determining any one or more parameters of the process and/or any one or more characteristics of the process) and with any suitable process monitoring techniques known in the art.

In some embodiments, the method includes estimating a probability that processes other than the last process performed on the patterned wafer before the output is acquired affect the noise map. In this manner, the method may include determining a probability that the currently observed signature has causes unrelated to the process step being monitored. The probability that the currently observed signature includes contributions from processes other than the last process performed on the patterned wafer may be determined in a number of manners. For instance, the probability may be determined based on information about the patterned wafer and the inspection system. Such information may include, for example, the transparency of the uppermost layer or layers on the patterned wafer to the wavelength(s) at which the inspection system operates, any pattern that is formed on the uppermost layer and underlying layers, one or more characteristics of the inspection system such as wavelength(s) of operation, type of inspection system or inspection mode (e.g., BF or DF), incidence angle, collection angle, etc. In addition, or alternatively, the probability may be determined based on information about the signatures corresponding to previous layers and the current layer. For example, the signatures that have been detected in noise maps and/or wafer images corresponding to previous processes performed on the wafer and an expected or "normal" signature for the current process may be used to determine if the noise map and/or wafer image for the current process includes contributions from the signatures for the previous processes. In one such example, if the previous processes are known to produce relatively strong signatures in noise maps and/or wafer images produced for those previous processes, the probability that the signatures for those processes will affect the noise map and/or wafer image for the current process may be relatively high.

In a further embodiment, the method includes identifying a signature in the noise map and estimating a degree to which signatures of processes other than the last process performed on the patterned wafer before the output is acquired contribute to the signature in the noise map based on optics of the inspection system used to acquire the output. In this manner, the method may include considering (through modeling or rules of thumb) the optics mode used to acquire the current and prior level images to estimate the degree to which previous level signatures could have contributed to the currently observed signatures. For example, rules of thumb such as whether some layers of a patterned wafer are relatively transparent to a particular optical configuration may be used to estimate the degree to which signatures of previous processes contribute to the currently observed process layer signature. In one such example, if the current layer of the patterned wafer is known to be relatively transparent to a particular optical configuration, the degree to which a previous process signature will affect the current process signature may be relatively high. In a similar manner, modeling of an inspection system optical configuration may be used (e.g., in combination with information about the current process performed on the wafer and/or previous process(es) performed on the wafer) to determine the degree to which the current layer of the wafer is transparent to the optical configuration. In one such example, if the modeling predicts that the current layer of the patterned wafer is relatively transparent to a particular optical configuration, the degree to which a previous process signature will affect the current process signature may be relatively high.

If the degree to which previous process signature(s) will affect the current process signature is relatively high, then the signature for the current process may be isolated from previous process signatures according to any of the embodiments described herein. In contrast, if the degree to which the previous process signature(s) will affect the current process signature is relatively low, then the signature for the current process may be extracted from the noise map and/or wafer image without regard to the previous process signature(s) (e.g., without first extracting the previous process signature(s) from the wafer image and/or noise map).

Any of the methods described above may include integration of design information (e.g., chip two-dimensional (2D) and/or three-dimensional (3D) design layout) or attributes extracted from the design information (e.g., attributes extracted from the layout such as pattern density, orientation, density gradients, etc.). For example, the method may include using the design information and any attributes of the design information to identify a signature corresponding to the last process in the noise map. In particular, the design for the layer of the wafer for which the output is acquired may affect the signature that is present in the noise map. Therefore, information about the design for the layer of the wafer for which the output is acquired may be used to identify the signature in the noise map. In a similar manner, if the design for the layer of the wafer for which the output is acquired is sufficiently different than the design for underlying layers of the wafer, the design for the layer for which the noise map is generated may be used to extract the signature for the current layer from the noise map.

Each of the embodiments of the method described above may include any other step(s) of any other method(s) described herein. In addition, each of the embodiments of the method described above may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after one or more of the images are generated as described herein, the method may include displaying the one or more images to a user. Furthermore, the results may be stored "permanently," "semi-permanently," temporarily, or for some period of time. For example, the storage medium may be random access memory (RAM), and the results may not necessarily persist indefinitely in the storage medium.

Further modifications and alternative embodiments of various aspects of the invention may be apparent to those skilled in the art in view of this description. For example, methods, carrier media, and systems for monitoring a characteristic of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for monitoring a characteristic of a specimen, comprising:
   determining a property of individual pixels on the specimen using output generated by inspecting the specimen with an inspection system;
   determining a characteristic of individual regions on the specimen using the properties of the individual pixels in the individual regions, wherein the characteristic of the individual regions comprises a statistic of the properties of the individual pixels within the individual regions;

determining the characteristic of the specimen, wherein the characteristic of the specimen comprises a specimen-level signature in the statistics for the individual regions;

monitoring the characteristic of the specimen based on the characteristics of the individual regions; and performing correlation analysis of the properties of the individual pixels in two or more die on the specimen to identify portions of the two or more die on the specimen in which the properties of the individual pixels are correlated as locations of a potential systematic defect causing mechanism on the specimen, wherein locations in the two or more die on the specimen at which the properties of the individual pixels vary indicate that geometries at the locations are not susceptible to a systematic defect causing mechanism.

2. The method of claim 1, wherein each of the individual regions has an area that is greater than an area of one individual pixel and is less than an area of the specimen.

3. The method of claim 1, wherein the individual regions have a rectangular shape, and wherein the individual regions form a two-dimensional grid on the specimen.

4. The method of claim 1, wherein the specimen comprises a patterned wafer.

5. The method of claim 1, further comprising identifying one or more of the individual regions having unique characteristics.

6. The method of claim 1, further comprising selecting one or more of the individual regions having unique characteristics for metrology.

7. The method of claim 1, further comprising determining one or more locations on the specimen corresponding to one or more of the individual regions having unique characteristics and generating information about the one or more locations that can be used to perform one or more measurements at the one or more locations.

8. The method of claim 1, wherein the characteristic of the specimen further comprises a die-level signature in the characteristics of the individual regions.

9. The method of claim 1, further comprising determining potential process problems based on the characteristics of the individual regions and generating output illustrating the potential process problems.

10. The method of claim 1, further comprising detecting defects on the specimen using the output while said monitoring is performed.

11. The method of claim 1, wherein the properties of the individual pixels used to determine the characteristic of each of the individual regions comprise the properties of all of the individual pixels within each of the individual regions.

12. The method of claim 1, wherein the characteristic of the individual regions further comprises a distribution of the properties of the individual pixels within the individual regions.

13. The method of claim 1, wherein the characteristic of the individual regions further comprises a property of a distribution of the properties of the individual pixels within the individual regions.

14. The method of claim 1, wherein the characteristic of the individual regions further comprises a property of a distribution of the properties of the individual pixels within the individual regions and a location corresponding to the property of the distribution.

15. The method of claim 1, wherein a portion of the individual regions corresponds to a die on the specimen, the method further comprising aligning the portion of the individual regions to a different portion of the individual regions corresponding to a different die on the specimen.

16. The method of claim 1, wherein a portion of the individual regions corresponds to a die on the specimen, the method further comprising aligning the portion of the individual regions to a reference die.

17. The method of claim 1, wherein different portions of the individual regions correspond to different dies on the specimen, the method further comprising aligning the different portions to a common reference grid.

18. The method of claim 1, wherein the property of the individual pixels comprises a differential between the properties of the individual pixels located in adjacent dies on the specimen at the same within die position, and wherein the characteristic of the individual regions further comprises a distribution of the differentials of the individual pixels within the individual regions.

19. The method of claim 1, wherein determining the characteristic of the individual regions comprises separating the individual pixels into groups based on design context associated with the individual pixels, and wherein the characteristic of the individual regions further comprises a characteristic of the groups.

20. The method of claim 1, further comprising generating output illustrating the property of each of the individual pixels corresponding to one of the individual regions as a function of position across the one of the individual regions.

21. The method of claim 1, further comprising comparing the properties of the individual pixels to a threshold value and generating output indicating the individual pixels on the specimen having a property that is above the threshold value and the individual pixels on the specimen having a property that is below the threshold value.

22. The method of claim 1, wherein the characteristic of the specimen further comprises the characteristic of the individual regions as a function of position across the specimen, and wherein said monitoring comprises determining similarities between the characteristic of the specimen and a reference.

23. The method of claim 1, wherein the characteristic of the specimen further comprises the characteristics of the individual regions corresponding to at least one die on the specimen combined with the characteristics of the individual regions corresponding to at least one additional die on the specimen.

24. The method of claim 1, wherein the characteristic of the specimen further comprises the characteristics of the individual regions corresponding to at least one die on the specimen combined with the characteristics of the individual regions corresponding to at least one additional die on the specimen, and wherein said monitoring comprises determining similarities between the combined characteristics and a reference.

25. The method of claim 1, wherein said monitoring comprises monitoring the characteristic of the specimen on a specimen-to-specimen basis or a lot-to-lot basis by comparing the characteristic of the specimen to one or more control limits.

26. The method of claim 1, wherein said monitoring comprises comparing the characteristic of the specimen to one or more control limits and determining additional locations on the specimen at which the characteristic of the specimen exceeds the one or more control limits, the method further comprising generating information about the additional locations that can be used to perform one or more measurements at the additional locations.

27. The method of claim 1, further comprising identifying different portions of die on the specimen having the same design context and determining if the properties of the individual pixels within the different portions having the same design context are correlated.

28. The method of claim 1, further comprising identifying different portions of die on the specimen having the same design context, determining if the properties of the individual pixels within the different portions having the same design context are correlated, and generating output illustrating the different portions having properties that are correlated.

29. The method of claim 1, wherein said monitoring comprises determining if the characteristics of the individual regions within two or more die on the specimen are correlated.

30. The method of claim 1, wherein said monitoring comprises identifying other portions of two or more die on the specimen in which the characteristics of the individual regions are correlated as locations of another potential systematic defect causing mechanism on the specimen.

31. The method of claim 1, wherein said monitoring comprises identifying different portions of die on the specimen having the same design context and determining if the characteristics of the individual regions within the different portions having the same design context are correlated.

32. The method of claim 1, wherein said monitoring comprises identifying different portions of die on the specimen having the same design context and determining if the characteristics of the individual regions within the different portions having the same design context are correlated, the method further comprising generating output illustrating the different portions having characteristics of the individual regions that are correlated.

33. The method of claim 1, further comprising stacking two or more individual dies on the specimen by overlaying the characteristics of the individual regions corresponding to the two or more individual dies and displaying a stacked die map.

34. The method of claim 1, further comprising constructing a signature image of the specimen, wherein each pixel of the signature image represents a selected characteristic of the individual regions.

35. The method of claim 34, further comprising displaying two or more signature images side by side.

36. The method of claim 34, further comprising displaying one or more signature images overlaid on a wafer map of defects.

37. A non-transitory computer-readable medium, comprising program instructions executable on a processor for performing a method for monitoring a characteristic of a specimen, wherein the method comprises:

determining a property of individual pixels on the specimen using output generated by inspecting the specimen with an inspection system;

determining a characteristic of individual regions on the specimen using the properties of the individual pixels in the individual regions, wherein the characteristic of the individual regions comprises a statistic of the properties of the individual pixels within the individual regions;

determining the characteristic of the specimen, wherein the characteristic of the specimen comprises a specimen-level signature in the statistics for the individual regions;

monitoring the characteristic of the specimen based on the characteristics of the individual regions; and performing correlation analysis of the properties of the individual pixels in two or more die on the specimen to identify portions of the two or more die on the specimen in which the properties of the individual pixels are correlated as locations of a potential systematic defect causing mechanism on the specimen, wherein locations in the two or more die on the specimen at which the properties of the individual pixels vary indicate that geometries at the locations are not susceptible to a systematic defect causing mechanism.

38. A system configured to monitor a characteristic of a specimen, comprising:

an inspection system configured to generate output by inspecting the specimen; and a processor configured to:

determine a property of individual pixels on the specimen using the output;

determine a characteristic of individual regions on the specimen using the properties of the individual pixels in the individual regions, wherein the characteristic of the individual regions comprises a statistic of the properties of the individual pixels within the individual regions;

determine the characteristic of the specimen, wherein the characteristic of the specimen comprises a specimen-level signature in the statistics for the individual regions;

monitor the characteristic of the specimen based on the characteristics of the individual regions; and perform correlation analysis of the properties of the individual pixels in two or more die on the specimen to identify portions of the two or more die on the specimen in which the properties of the individual pixels are correlated as locations of a potential systematic detect causing mechanism on the specimen, wherein locations in the two or more die on the specimen at which the properties of the individual pixels vary indicate that geometries at the locations are not susceptible to a systematic defect causing mechanism.

* * * * *